(12) United States Patent
Lund

(10) Patent No.: US 12,084,715 B1
(45) Date of Patent: Sep. 10, 2024

(54) METHODS AND SYSTEMS FOR REDUCING ARTIFACTUAL ANTISENSE PRODUCTS

(71) Applicant: 10x Genomics, Inc., Pleasanton, CA (US)

(72) Inventor: Paul Eugene Lund, San Leandro, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 284 days.

(21) Appl. No.: 17/518,213

(22) Filed: Nov. 3, 2021

Related U.S. Application Data

(60) Provisional application No. 63/110,104, filed on Nov. 5, 2020.

(51) Int. Cl.
| | | |
|---|---|---|
| C12Q 1/68 | (2018.01) | |
| C12Q 1/6806 | (2018.01) | |
| C12Q 1/6848 | (2018.01) | |

(52) U.S. Cl.
CPC ......... *C12Q 1/6848* (2013.01); *C12Q 1/6806* (2013.01)

(58) Field of Classification Search
None
See application file for complete search history.

(56) References Cited

U.S. PATENT DOCUMENTS

| | | |
|---|---|---|
| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Co-pending U.S. Appl. No. 18/392,684, inventors Fernandes; Sunjay Jude et al., filed on Dec. 21, 2023.

(Continued)

*Primary Examiner* — Aaron A Priest
(74) *Attorney, Agent, or Firm* — Wilson Sonsini Goodrich & Rosati

(57) ABSTRACT

Disclosed herein is a method of preventing the amplification of artifactual antisense products when sequencing a target polynucleotide. Incorporation of modified nucleotides into handle polynucleotide sequences can allow for the selective degradation of artifact antisense products generated by mis-priming, prior to amplification, thus preventing them from appearing in the amplification library. Selective degradation can be accomplished using one or more agents configured to specifically cleave the handle polynucleotide at the modified nucleotide. Amplification can be performed using a primer that is configured to hybridize to the handle sequence and a second primer that is configured to hybridize to a complement of a target nucleotide.

27 Claims, 17 Drawing Sheets

Specification includes a Sequence Listing.

(56) References Cited

U.S. PATENT DOCUMENTS

| | | |
|---|---|---|
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,265,552 B1 | 7/2001 | Schatz |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagilov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,450,607 B2 | 10/2019 | Hindson et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,550,429 B2 | 2/2020 | Harada et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,952,626 B2 | 4/2024 | Pfeiffer et al. |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |

(56) References Cited

U.S. PATENT DOCUMENTS

| | | |
|---|---|---|
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0330694 A1 | 10/2019 | Schnall-Levin |
| 2019/0345636 A1 | 11/2019 | McDermott et al. |
| 2019/0352717 A1 | 11/2019 | Schnall-Levin |
| 2019/0367969 A1 | 12/2019 | Belhocine et al. |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0131564 A1* | 4/2020 | Jiang ............... G16B 40/10 |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2023/0193254 A1* | 6/2023 | Isakova ............... C12Q 1/6806 435/6.12 |
| 2024/0002914 A1 | 1/2024 | Pfeiffer |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |

(56) References Cited

FOREIGN PATENT DOCUMENTS

| | | |
|---|---|---|
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018075693 A1 | 4/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

10X Genomics, Inc. CG000153 Rev A. Chromium Single Cell DNA Reagent Kits User Guide. 2018.

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate, A.R. et al. "Beating Poisson encapsulation statistics using close-packed ordering" Lab on a Chip (Sep. 21, 2009) 9(18):2628-2631.

Adamson et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Braeckmans et al., Scanning the Code. Modern Drug Discovery. 2003:28-32.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Buchman GW, et al. Selective RNA amplification: a novel method using dUMP-containing primers and uracil DNA glycosylase. PCR Methods Appl. Aug. 1993; 3(1):28-31.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-15. Epub Aug. 9, 2001.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chien et al. "Multiport flow-control system for lab-on-a-chip microfluidic devices", Fresenius J. Anal Chem, 371:106-111 (Jul. 27, 2001).

Chu, et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Co-pending U.S. Appl. No. 16/434,076, inventor Giresi; Paul, filed on Jun. 6, 2019.

Co-pending U.S. Appl. No. 16/434,084, inventor Giresi; Paul, filed on Jun. 6, 2019.

Co-pending U.S. Appl. No. 16/434,102, inventors Price; Andrew D. et al., filed on Jun. 6, 2019.

Co-pending U.S. Appl. No. 16/737,762, inventors Price; Andrew D. et al., filed on Jan. 8, 2020.

(56) References Cited

OTHER PUBLICATIONS

Co-pending U.S. Appl. No. 16/737,770, inventors Belhocine; Zahara Kamila et al., filed on Jan. 8, 2020.
Co-pending U.S. Appl. No. 16/789,273, inventors Maheshwari; Arundhati Shamoni et al., filed on Feb. 12, 2020.
Co-pending U.S. Appl. No. 16/800,450, inventor Katherine; Pfeiffer, filed on Feb. 25, 2020.
Co-pending U.S. Appl. No. 17/014,909, inventor Giresi; Paul, filed on Sep. 8, 2020.
Co-pending U.S. Appl. No. 17/148,942, inventors McDermott; Geoffrey et al., filed on Jan. 14, 2021.
Co-pending U.S. Appl. No. 17/166,982, inventors McDermott; Geoffrey et al., filed on Feb. 3, 2021.
Co-pending U.S. Appl. No. 17/175,542, inventors Maheshwari; Arundhati Shamoni et al., filed on Feb. 12, 2021.
Co-pending U.S. Appl. No. 17/220,303, inventor Walter; Dagmar, filed on Apr. 1, 2021.
Co-pending U.S. Appl. No. 17/318,364, inventors Bava; Felice Alessio et al., filed on May 12, 2021.
Co-pending U.S. Appl. No. 17/381,612, inventor Martinez; Luigi Jhon Alvarado, filed on Jul. 21, 2021.
Co-pending U.S. Appl. No. 17/512,241, inventors Hill; Andrew John et al., filed on Oct. 27, 2021.
Co-pending U.S. Appl. No. 17/517,408, inventors Salmanzadeh; Alireza et al., filed on Nov. 2, 2021.
Co-pending U.S. Appl. No. 17/522,741, inventors Zheng; Xinying et al., filed on Nov. 9, 2021.
Co-pending U.S. Appl. No. 17/545,862, inventor Katherine; Pfeiffer, filed on Dec. 8, 2021.
Co-pending U.S. Appl. No. 17/573,350, inventor Corey; M. Nemec, filed on Jan. 11, 2022.
Co-pending U.S. Appl. No. 17/580,947, inventor Gibbons; Michael, filed on Jan. 21, 2022.
Co-pending U.S. Appl. No. 17/957,781, inventor Bava; Felice Alessio, filed on Sep. 30, 2022.
Co-pending U.S. Appl. No. 18/046,843, inventor Toh; Mckenzi, filed on Oct. 14, 2022.
Co-pending U.S. Appl. No. 18/152,650, inventor Shastry; Shankar, filed on Jan. 10, 2023.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecule DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9): e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidically generated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.

(56) References Cited

OTHER PUBLICATIONS

Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL: http://454.com/downloads/my454/documentation/technical-bulletins/TCB-09004 UsingMultiplexIdentifierAdaptorsForTheGSFLXTitan iumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)"107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.

* cited by examiner

```
                              SEQUENCE LISTING

<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(15)
<223> OTHER INFORMATION: Any modified a, c, t, or g
<220> FEATURE:
<221> NAME/KEY: modified_base
<222> LOCATION: (20)..(20)
<223> OTHER INFORMATION: Any modified a, c, t, or g
<220> FEATURE:
<221> NAME/KEY: modified_base
<222> LOCATION: (23)..(47)
<223> OTHER INFORMATION: a, c, t, g, unknown or other

<400> SEQUENCE: 1
ctacacgacg ctcnnccgan ctnnnnnnnn nnnnnnnnnn nnnnnnnttt cttatatggg      60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(47)
<223> OTHER INFORMATION: a, c, t, g, unknown or other

<400> SEQUENCE: 2
ctacacgacg ctcttccgat ctnnnnnnnn nnnnnnnnnn nnnnnnnttt cttatatggg      60

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaaaaaa                                                 20

<210> SEQ ID NO 4
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
```
aaaaaaaaaa aaaa                                                14

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aaaaaa                                              16

<210> SEQ ID NO 6
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaaaaaaa a                                                   11

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttttttttt ttt                                                 13

<210> SEQ ID NO 8
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa aa                                                  12

METHODS AND SYSTEMS FOR REDUCING ARTIFACTUAL ANTISENSE PRODUCTS

CROSS-REFERENCE TO RELATED APPLICATIONS

Sequence Listing

This application includes a Sequence Listing submitted electronically as an ASCII file created on Jan. 28, 2022, named 10416_066US1_SL.txt which is 2,679 bytes in size and is hereby incorporated by reference in its entirety.

This application claims priority or the benefit of U.S. Provisional Patent Application 63/110,104, filed Nov. 5, 2020, the contents of which are fully incorporated herein by reference.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed. Samples in partitions may contain deoxyribonucleic acid molecules or ribonucleic acid molecules which a processed by polymerase chain reaction as part of a sequencing analysis.

Artifactual antisense reads can be generated at a high rate in high throughput sequencing technologies. Antisense reads can be discarded as "wasted data", which can ultimately result in increased sequencing costs. The negative impact of antisense reads on sequencing efficiency can be exacerbated due to an inability of presently available pull-down strategies to discriminate between genuine and mis-primed antisense library fragments. The present disclosure provides a solution by preventing the amplification of artifactual antisense products.

SUMMARY

Disclosed herein is a method of preventing the amplification of artifactual antisense products. By incorporating modified nucleotides into handle polynucleotide sequences, artifact antisense products generated by mis-priming can be selectively degraded prior to amplification, thus preventing them from appearing in the amplification library. Selective degradation can be accomplished using one or more agents configured to specifically cleave the handle polynucleotide at the modified nucleotide. Amplification is then performed using a primer that is configured to hybridize to the handle sequence and a second primer that is configured to hybridize to a complement of a target nucleotide.

Disclosed herein is a method of nucleic acid processing, comprising providing a nucleic acid strand comprising a nucleic acid sequence associated with a barcode nucleic acid strand, wherein said barcode nucleic acid strand comprises a handle sequence comprising a sequence complementary to a first primer binding sequence and wherein said nucleic acid strand comprises a sequence complementary to a second primer binding sequence; extending said nucleic acid strand using said handle sequence of said barcode nucleic acid strand as a template to produce an extension product comprising said nucleic acid sequence and said first primer binding sequence; cleaving said handle sequence of said barcode nucleic acid strand; and amplifying said nucleic acid sequence using said extension product, a polymerase, a first primer that is hybridizable to said first primer binding sequence, and a second primer that is hybridizable to said second primer binding sequence to produce an amplification product comprising said nucleic acid sequence.

The handle sequence can comprise one or more modified nucleotides, wherein said cleaving occurs at said one or more modified nucleotides. The one or more modified nucleotides can be selected from the group consisting of deoxy uracil, thymine glycol, deoxyuridine, 5,6-dihydroxythymine, 5-hydroxy-5-methylhydantoin, uracil glycol, 6-hydroxy-5,6-dihydrothymine, 7,8-dihydro-8-oxoguanine (8-oxoguanine), 8-oxoadenine, fapy-guanine, methyl-fapy-guanine, fapyadenine, aflatoxin B1-fapy-quanine, 5-hydroxy-cytosine, 5-hydroxyuracil, 5-hydroxymethyluracil, 5-formyluracil, is-syn cyclobutene pyrimidine dimer(s), 5,6-dihydrothymine, 5,6-dihydroxyuracil, 4,6-diamino-5-formamidopyrimidine, and 2,6-diamino-4-hydroxy-5-formamidopyrimidine." The cleaving can be performed using a cleaving agent. The cleaving agent can comprise a temperature dependent cleaving agent. The cleaving agent can be an enzyme selected from the group consisting of: uracil-DNA glycosylase (UDG), endonuclease VIII, Afu Uraci-DNA Glycosylase (UDG), antarctic thermolabile UDG, Tma endonuclease III, endonuclease IV, Tth endonuclease IV, endonuclease V, formamidopyrimidine DNA glycosylase (Fpg), human alkyl adenine DNA glycosylase (hAAG), hSMUG1, T4 PDG (T4 endonuclease V), hNEIL1, and hOGG1. The cleaving agent can be formamidopyrimidine DNA glycosylase (Fpg) and said one or more modified nucleotides can be selected from the group comprising: 7,8-dihydro-8-oxoguanine (8-oxoguanine), 8-oxoadenine, fapy-guanine, fapy-adenine, aflatoxin, methyl-fapy-guanine, fapy-adenine, aflatoxin B1-fapy-guanine, 5-hydroxy-cytosine, and 5-hydroxy-uracil. The cleaving agent can be human alkyl adenine DNA glycosylase (hAAG) and said one or more modified nucleotides can be selected from the group comprising: 3-methyladenine, 7-methylguanine 1, N6-ethenoadenine, hypoxanthine, deoxyinosine, and deoxyxanthosine. The cleaving agent can comprise a temperature dependent cleaving agent. The cleaving agent can be inactivated at a temperature greater than 65 degrees Celsius. The cleaving agent can comprise one or more enzymes.

The handle sequence can comprise one or more modified nucleotides, wherein said cleaving occurs at said one or more modified nucleotides. One or more enzymes can comprise uracil DNA glycosylase (UDG) and endonuclease VIII or endonuclease III. One or more modified nucleotides can be selected from the group consisting of: deoxyuridine, urea, 5,6 dihydroxythymine, thymine glycol, 5-hydroxy-5-methylhydantoin, uracil glycol, 6-hydroxy-5, 6-dihydrothymine, and methylartonylurea. The enzyme can comprise an N-glycosylase. The enzyme can comprise an AP-lyase. The nucleic acid strand can be a complementary DNA (cDNA) strand.

The nucleic acid strand can be associated with said barcode nucleic acid strand via a template switching sequence. The cDNA strand can be a reverse transcription product of a target RNA molecule. The cDNA strand can comprise a template switching sequence. In some embodiments, (b) can occur before (c) and (d). Providing said nucleic acid strand associated with said barcode nucleic acid strand can comprise partitioning said barcode nucleic acid strand and a template RNA molecule from a cell into a partition.

The barcode nucleic acid strand can be releasably attached to a bead, optionally wherein said barcode nucleic acid strand is releasably attached to said bead via a releasable linkage. The bead can be a gel bead. The releasable linkage is configured to release upon exposure to a stimulus. The stimulus can comprise temperature, pH, pressure, a photo stimulus, or a chemical stimulus. The method can further comprise exposing said releasable linkage to said stimulus. The method can further comprise reverse transcribing said template RNA molecule. Reverse transcribing can occur after said barcode nucleic acid strand has been released from said bead. In some embodiments, (c) occurs simultaneously with (d). In some embodiments, (d) occurs after (c). The barcode nucleic acid strand can comprise a template switching sequence. The method can further comprise sequencing said product. The method can comprise providing said nucleic acid strand associated with said barcode nucleic acid strand in a partition in (a). The partition can be a droplet. The partition can be a well. The barcode nucleic acid strand can comprise a barcode sequence. The barcode nucleic acid strand can comprise a unique molecular identifier (UMI) sequence.

Disclosed herein is a system comprising a reaction volume, comprising a nucleic acid molecule a barcode nucleic acid molecule comprising a sequence complementary to a sequence of said nucleic acid molecule and a handle sequence, wherein said handle sequence comprises a modified nucleotide; and a cleaving agent configured to cleave said handle sequence of said barcode nucleic acid molecule at said modified nucleotide. The handle sequence can be at a 5' end of said barcode nucleic acid molecule and the sequence complementary to a sequence of said nucleic acid molecule can be at a 3' end of said barcode nucleic acid molecule. The cleaving agent can be within a bead.

The barcode nucleic acid molecule can be attached to a bead via said handle sequence. The bead can be a gel bead. The bead can be configured to release the cleaving agent into the partition upon application of a stimulus. The stimulus can comprise an ion concentration, a temperature change, a pH change, a reducing agent, a light stimulus, an electrical stimulus, or a magnetic stimulus.

The nucleic acid molecule can be a complementary DNA (cDNA) molecule. The cDNA molecule can be a reverse transcription product of a target RNA molecule. The reaction volume can be a droplet.

Disclosed herein is a kit comprising a barcode nucleic acid molecule comprising a barcode sequence, a sequence complementary to a sequence of a nucleic acid molecule and a handle sequence at a 5' end of said barcode nucleic acid barcode, wherein said handle sequence comprises said modified nucleotide; and a cleaving agent configured to cleave said handle sequence at said modified nucleotide. The modified nucleotide can be selected from the group consisting of deoxy uracil and thymine glycol. The cleaving agent can comprise an enzyme. The enzyme can comprise uracil DNA glycosylase (UDG) and endonuclease VIII. The enzyme can comprise an N-glycosylase. The enzyme can comprise an AP-lyase. The nucleic acid molecule can be a complementary DNA (cDNA) molecule. The cDNA molecule can be a reverse transcription product of a target RNA molecule.

The barcode nucleic acid barcode can be attached to a bead via said handle sequence. The bead can be a gel bead. The cleaving agent can be within said bead. The bead can be configured to release said cleaving agent upon exposure to a stimulus. The stimulus can comprise a change in temperature, a change in pH, a change in pressure, a photo stimulus, or a chemical stimulus.

Disclosed herein is a composition comprising a barcode nucleic acid molecule comprising a template switching sequence and a handle sequence at a 5' end of the barcode nucleic acid molecule, wherein the handle sequence comprises one or more modified nucleotides, wherein the handle sequence is configured to be cleaved at the one or more modified nucleotides. The handle sequence can be configured to be cleaved using uracil DNA glycosylase (UDG) and endonuclease VIII. The barcode nucleic acid molecule can be attached to a bead. The bead can comprise a cleaving agent. The bead can be configured to release the cleavage enzyme upon application of a stimulus.

Disclosed herein is a kit comprising a barcode nucleic acid molecule comprising a barcode sequence, a sequence complementary to a sequence of a nucleic acid molecule and a handle sequence at a 5' end of said barcode nucleic acid barcode, wherein said handle sequence comprises said modified nucleotide; and a cleaving agent configured to cleave said handle sequence at said modified nucleotide. The modified nucleotide can be selected from the group consisting of deoxy uracil and thymine glycol. The cleaving agent can comprise an enzyme. The enzyme can comprise uracil DNA glycosylase (UDG) and endonuclease VIII. The enzyme can comprise an N-glycosylase. The enzyme can comprise an AP-lyase. The nucleic acid molecule can be a complementary DNA (cDNA) molecule. The cDNA molecule can be a reverse transcription product of a target RNA molecule. The barcode nucleic acid barcode can be attached to a bead via said handle sequence. The bead can be a gel bead. The cleaving agent can be within said bead. The bead can be configured to release said cleaving agent upon exposure to a stimulus. The stimulus can comprise temperature, pH, pressure, a photo stimulus, or a chemical stimulus.

Disclosed herein is a composition comprising a barcode nucleic acid molecule comprising a template switching sequence and a handle sequence at a 5' end of said barcode nucleic acid molecule, wherein said handle sequence comprises one or more modified nucleotides, wherein said handle sequence is configured to be cleaved at said one or more modified nucleotides. The handle sequence can be configured to be cleaved using uracil DNA glycosylase (UDG) and endonuclease VIII. The barcode nucleic acid molecule can be attached to a bead. The bead can comprise a cleaving agent. The bead can be configured to release said cleavage enzyme upon application of a stimulus.

Disclosed herein is a kit comprising a barcode nucleic acid strand comprising a handle sequence and instructions to direct the user to provide a nucleic acid strand hybridized to said barcode nucleic acid strand; use said nucleic acid strand hybridized to said barcode nucleic acid strand to produce an extension product comprising said nucleic acid strand and a sequence complementary to said handle sequence; cleave said handle sequence of said barcode nucleic acid strand; and expose said extension product to a polymerase enzyme, a first primer that is complementary to a complement of said handle sequence, and a second primer that is complementary to said nucleic acid strand to produce a product comprising a sequence of said extension product.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7 discloses SEQ ID NOs: 3, 4, 4, and 4, respectively, in order of appearance.

FIG. 10 discloses SEQ ID NOs: 4, 5, and 5, respectively, in order of appearance.

FIG. 12B discloses SEQ ID NOs: 6, 7, 6, and 7, respectively, in order of appearance. FIG. 12C discloses SEQ ID NO: 6.

FIG. 15 discloses SEQ ID NOs: 4, 4, 8, and 4, respectively, in order of appearance.

FIG. 16 discloses SEQ ID NOs: 3, 3, 3, and 3, respectively in order of appearance.

DETAILED DESCRIPTION

Figure 1:
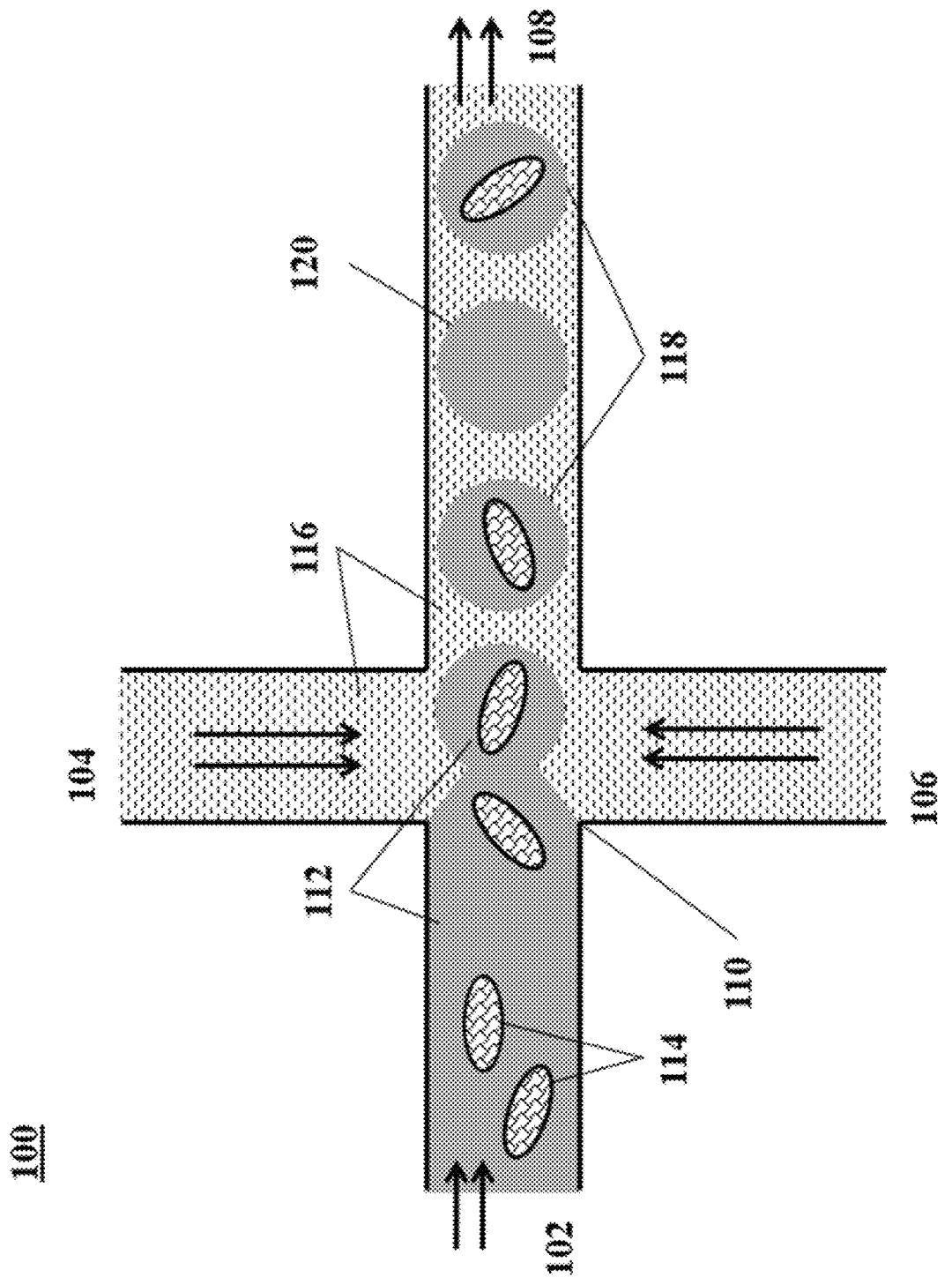
FIG. 1 shows an example of a microfluidic channel structure for partitioning individual analyte carriers.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. The nucleic acid barcode molecule may be coupled to or attached to the nucleic acid molecule comprising the nucleic acid sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction may be performed prior to, during, or following barcoding of the nucleic acid sequence to generate the barcoded nucleic acid molecule. For example, the nucleic acid molecule comprising the nucleic acid sequence may be subjected to reverse transcription and then be attached to the nucleic acid barcode molecule to generate the barcoded nucleic acid molecule, or the nucleic acid molecule comprising the nucleic acid sequence may be attached to the nucleic acid barcode molecule and subjected to a nucleic acid reaction (e.g., extension, ligation) to generate the barcoded nucleic acid molecule. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the nucleic acid molecule (e.g., mRNA).

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "analyte carrier," as used herein, generally refers to a discrete biological system derived from a biological sample. The analyte carrier may be or comprise a biological particle. The analyte carrier may be a macromolecule. The analyte carrier may be a small molecule. The analyte carrier may be a virus. The analyte carrier may be a cell or derivative of a cell. The analyte carrier may be an organelle. The analyte carrier may be a rare cell from a population of cells. The analyte carrier may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The analyte carrier may be a constituent of a cell. The analyte carrier may be or may include DNA, RNA, organelles, proteins, or any combination thereof. The analyte carrier may be or may include a matrix (e.g., a gel or polymer matrix) comprising a cell or one or more constituents from a cell (e.g., cell bead), such as DNA, RNA, organelles, proteins, or any combination thereof, from the cell. The analyte carrier may be obtained from a tissue of a subject. The analyte carrier may be a hardened cell. Such hardened cell may or may not include a cell wall or cell membrane. The analyte carrier may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix. A biological particle may comprise or be an analyte carrier. As such, the terms "analyte carrier" and "biological particle" may be used interchangeably herein.

The term "macromolecular constituent," as used herein, generally refers to a macromolecule contained within or from an analyte carrier or biological particle. The macromolecular constituent may comprise a nucleic acid. In some cases, the analyte carrier may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Systems and Methods for Improved Nucleotide Amplification

Provided herein are systems and methods for reducing or preventing the amplification of artifactual antisense nucleic acid sequences in high-throughput sequencing. Artifactual antisense nucleic acid sequences can result from the mispriming of barcode nucleic acid strands to target mRNA molecules prior to reverse transcription. In an aspect, the present disclosure provides for the selective degradation of an nucleic acid molecule comprising a barcode sequence.

Figure 16:
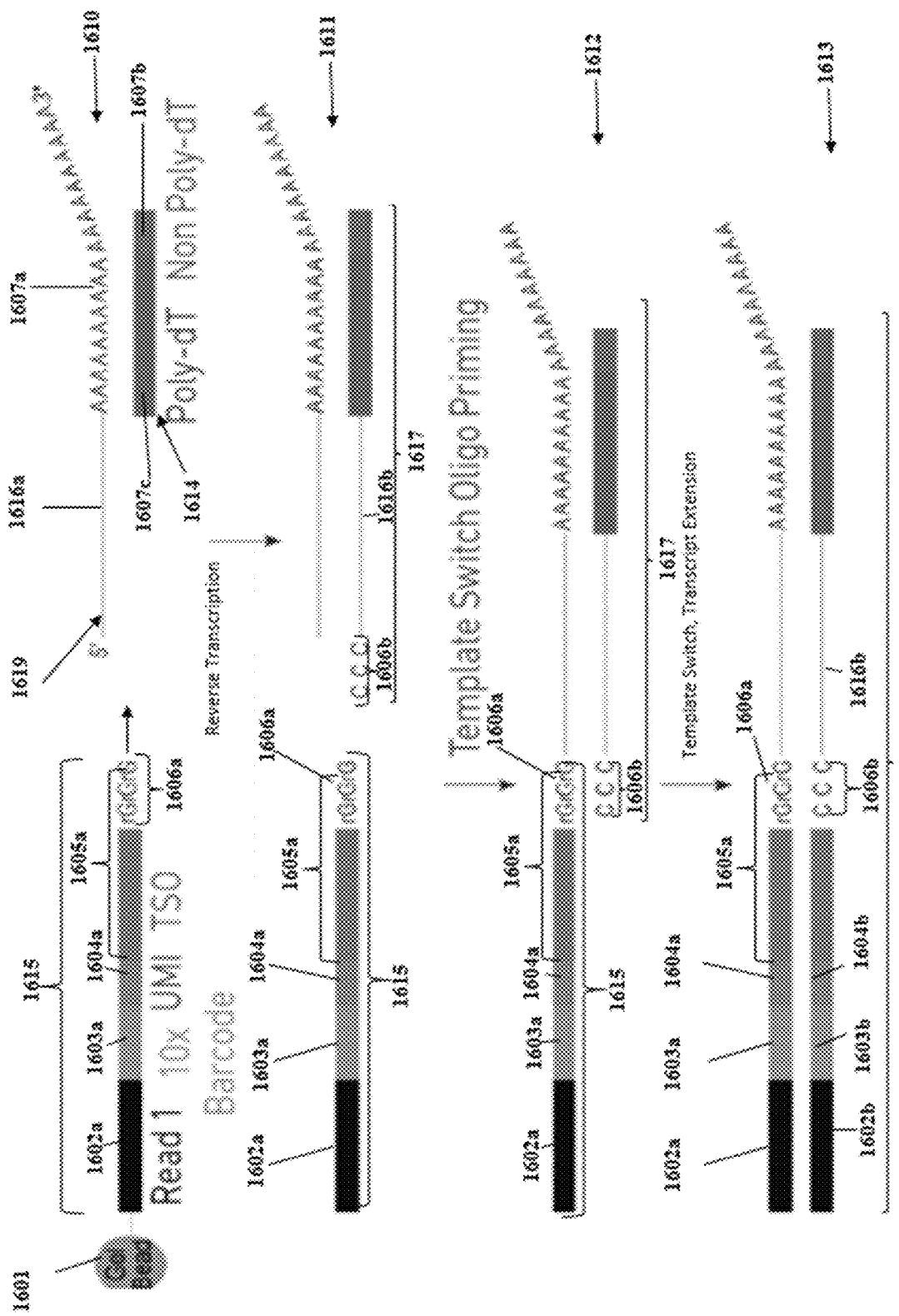
FIG. 16 illustrates the expected priming between a barcode nucleotide and a target polynucleotide resulting in an expected extension product.

FIG. 16 illustrates an example of a process by which a barcode nucleic acid strand can prime to a target nucleic acid molecule resulting in an expected extension product. As can be seen in FIG. 16 a barcode nucleic acid strand 1615 can be provided. The barcode nucleic acid strand 1615 can be releasably attached to a bead 1601. The barcode nucleic acid strand 1615 can comprise a handle sequence 1602a, a barcode sequence 1603a, a unique molecular identifier 1604a and/or a template switching sequence 1605a that can further comprise a rGrGrG sequence 1606a configured to associate to a template switching sequence 1606b (e.g., CCC sequence) of a cDNA molecule. In step 1610, a reverse transcription primer 1614 comprising a poly-dT sequence 1607c and a non-poly-dT sequence 1607b anneals to a target nucleic acid molecule 1619. The target nucleic acid molecule 1619 can be an mRNA molecule comprising a target sequence 1616a and a poly-A tail 1607a. In step 1611, the reverse transcription primer 1614 can be extended along the length of the target nucleic acid molecule to produce a reverse transcription product 1617. The reverse transcription product 1617 comprises a sequence complementary to the target nucleic acid sequence 1616b and a template switching sequence 1606b. In step 1612, the reverse transcription product 1617 can be associated with a template switching sequence 1606a of the barcode nucleic acid molecule 1615. In step 1613, the reverse transcription product 1617 is extended to produce a first extension product 1619 that can include a complement of the barcode nucleic acid molecule 1615.

Figure 7:
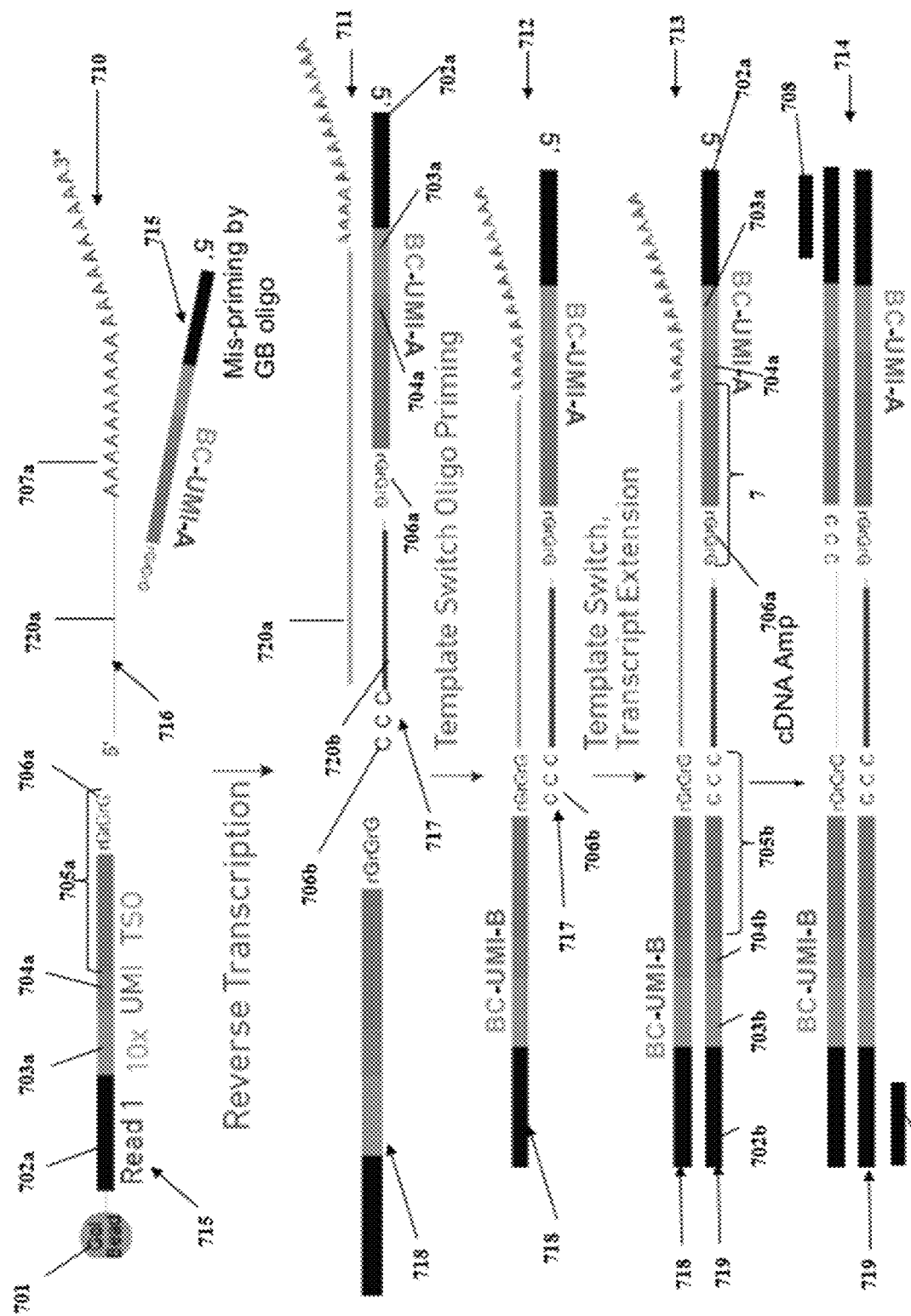
FIG. 7 illustrates mis-priming between barcode nucleotide and a target polynucleotide resulting in a first extension product capable of associating with a second handle sequence to produce an extension product comprising a handle sequence at both a 5' end and a 3' end of the extension product.

FIG. 7 illustrates an example of a process by which a barcode nucleic acid strand can mis-prime to a target nucleic acid molecule resulting in a mis-primed extension product comprising a handle sequence at both a 5' end and 3' end of the mis-primed extension product. As can be seen in FIG. 7, a barcode nucleic acid strand 715 can be provided. The barcode nucleic acid strand 715 can be releasably attached to a bead 701. The barcode nucleic acid strand 715 can comprise a handle sequence 702a, a barcode sequence 703a, a unique molecular identifier 704a and/or a template switching sequence 705a that can further comprise a rGrGrG sequence 706a configured to associate to a CCC sequence of a cDNA molecule. In step 710, the barcode nucleic acid strand 715 can be released from the bead 701 and can mis-prime to a target nucleic acid molecule 716. The target nucleic acid molecule 716 can be an mRNA molecule comprising a target sequence 720a and a poly-A tail 707a. In step 711, the misprimed barcode nucleic acid strand 715 can be extended to produce a first mis-primed extension product 717 that can include a complement of at least a portion of the target sequence 720b, and a CCC sequence 706b at a 3' end of the extension product. In step 712, the first mis-primed extension product 717 can be associated with a second barcode nucleic acid strand 718. In step 713, the extension product 717 can be extended to produce a second mis-primed extension product 719 that can include a complement (702b, 703b, 704b, 705b) of the second barcode nucleic acid strand 718 which comprises a different UMI sequence (e.g., BC-UMI-B) than the first barcode nucleic acid strand 715 (e.g., BC-UMI-A) In Step 714, the second mis-primed extension product 719 can be amplified using primers (708) that are complementary to the handle sequence.

Figure 8:
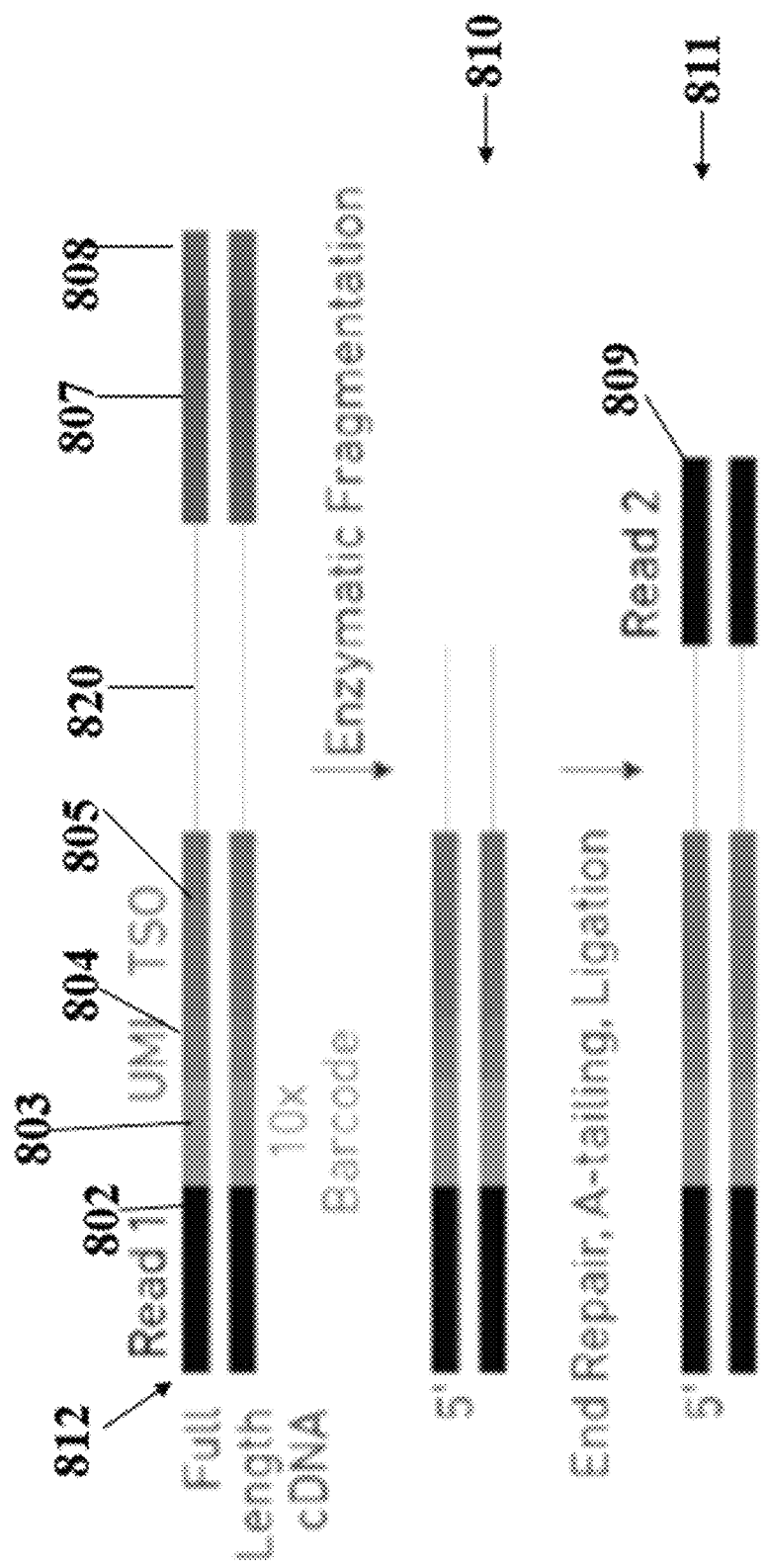
FIG. 8 illustrates the fragmentation of an amplified extension product that has primed correctly.

FIG. 8 illustrates an example of post-amplification processing of an extension product nucleic acid molecule. The extension product nucleic acid molecule can comprise a handle sequence 802, a barcode sequence 803, a unique molecular identifier 804, a template switching sequence 805, a target sequence 820, a poly-dT sequence 807, and/or an amplification sequence 808. In step 810, the poly-dT sequence 807 and the amplification sequence 808 can be removed from the extension product oligonucleotide by enzyme fragmentation. In step 811, a functional sequence 809 can be ligated to the target sequence 820 for further sequencing steps.

Figure 9:
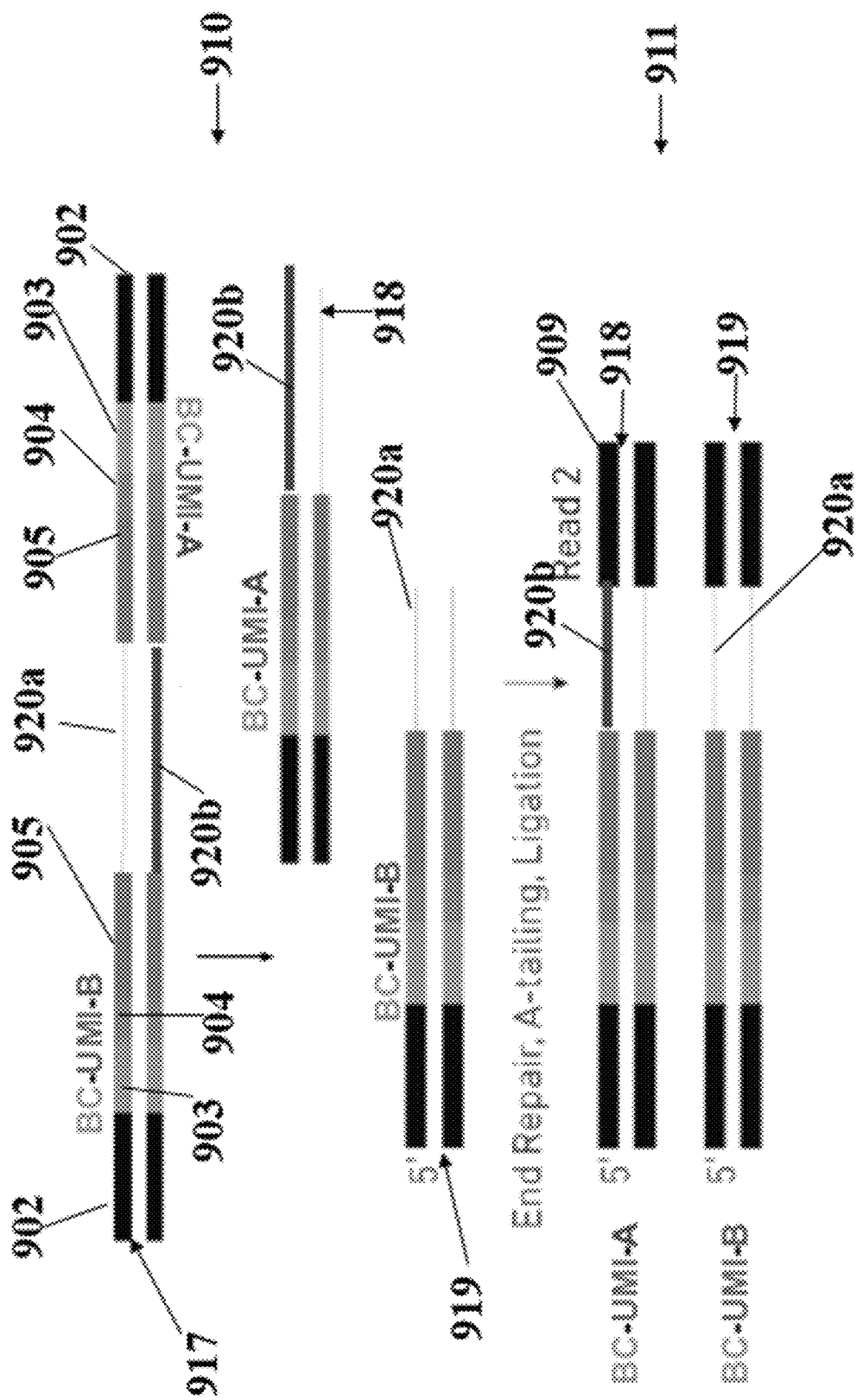
FIG. 9 illustrates the fragmentation of the mis-primed extension product of FIG. 7.

FIG. 9 illustrates an example of post-amplification processing of a mis-primed extension product nucleic acid molecule 917. The mis-primed extension product nucleic acid molecule 917 can comprise two handle sequences 902, two barcode sequences 903, two unique molecular identifiers 904, two template switching sequences 905, and/or a target sequence (920a, 920b). In step 910, the mis-primed extension product oligonucleotide 917 can be cleaved at a template switching sequence 905 and can undergo end repair, resulting in two distinct nucleic acid molecules with handle sequences, 918 and 919. An antisense cleavage product nucleic acid molecule, 918, can comprise a complement of the target sequence 920b, which will be read in further sequencing processes as an anti-sense product. The antisense cleavage product nucleic acid molecule 918 is not a true antisense product, but is an artifact of the mis-priming that resulted in the mis-primed extension product nucleic acid molecule 917. A sense cleavage product nucleic acid molecule 919 can comprise the target sequence 920a, which can be read in further sequencing processes as a sense product. In step 911, the two distinct nucleic acid molecules with handle sequences (918 and 919), can be ligated to a functional nucleic acid molecule 909 at the target sequence 920a and the complement of the target sequence 920b, respectively. The functional nucleic acid molecule 909 can comprise a functional sequence for further sequencing processes. The functional sequence can be configured to attach to a sequencing flow cell. Thus, both the artifactual antisense product 918 and the true sense product 919 are present in the sequencing run.

Figure 10:
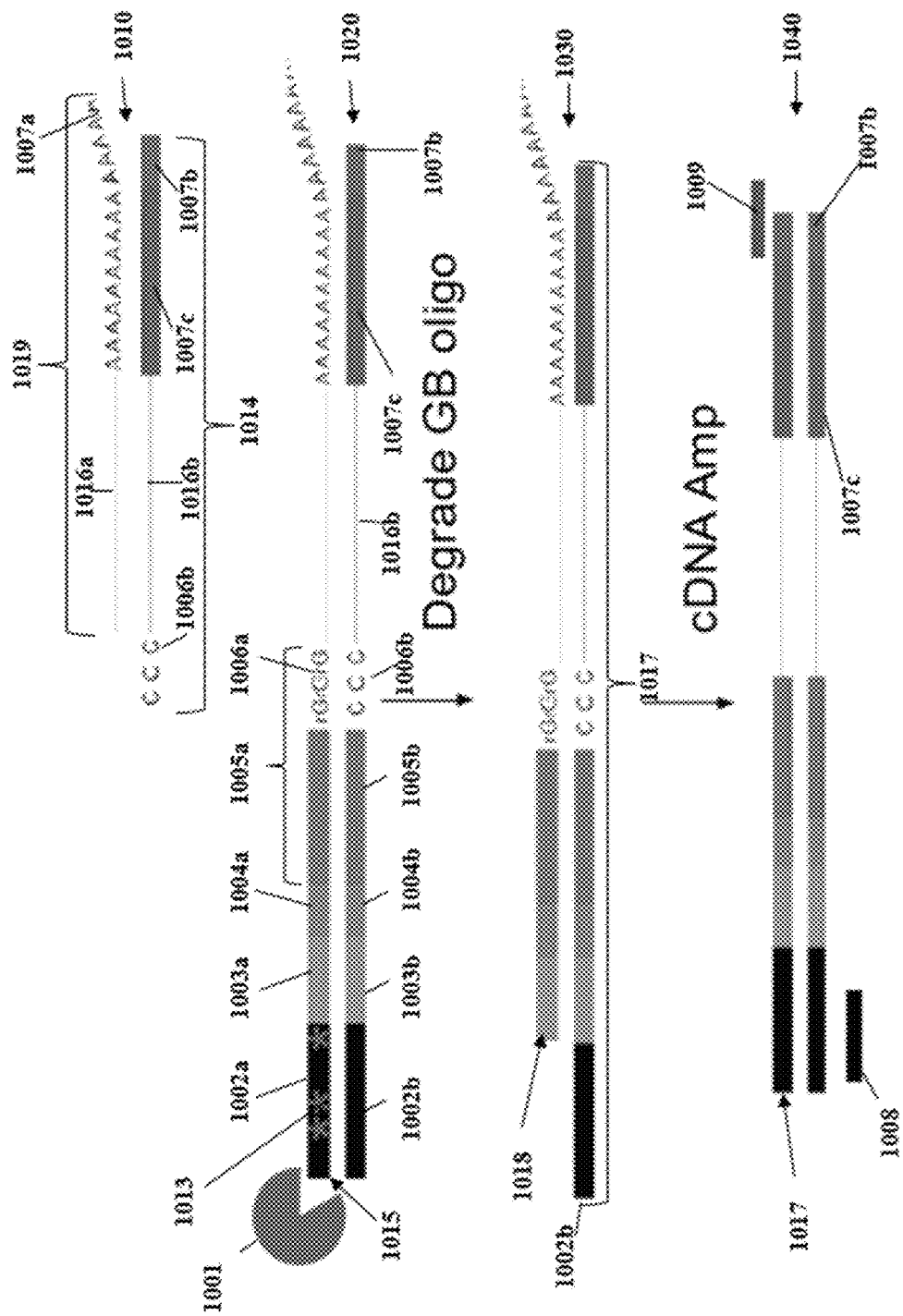
FIG. 10 illustrates the selective degradation of a handle sequence after the production of a correctly transcribed extension product.
Figure 15:
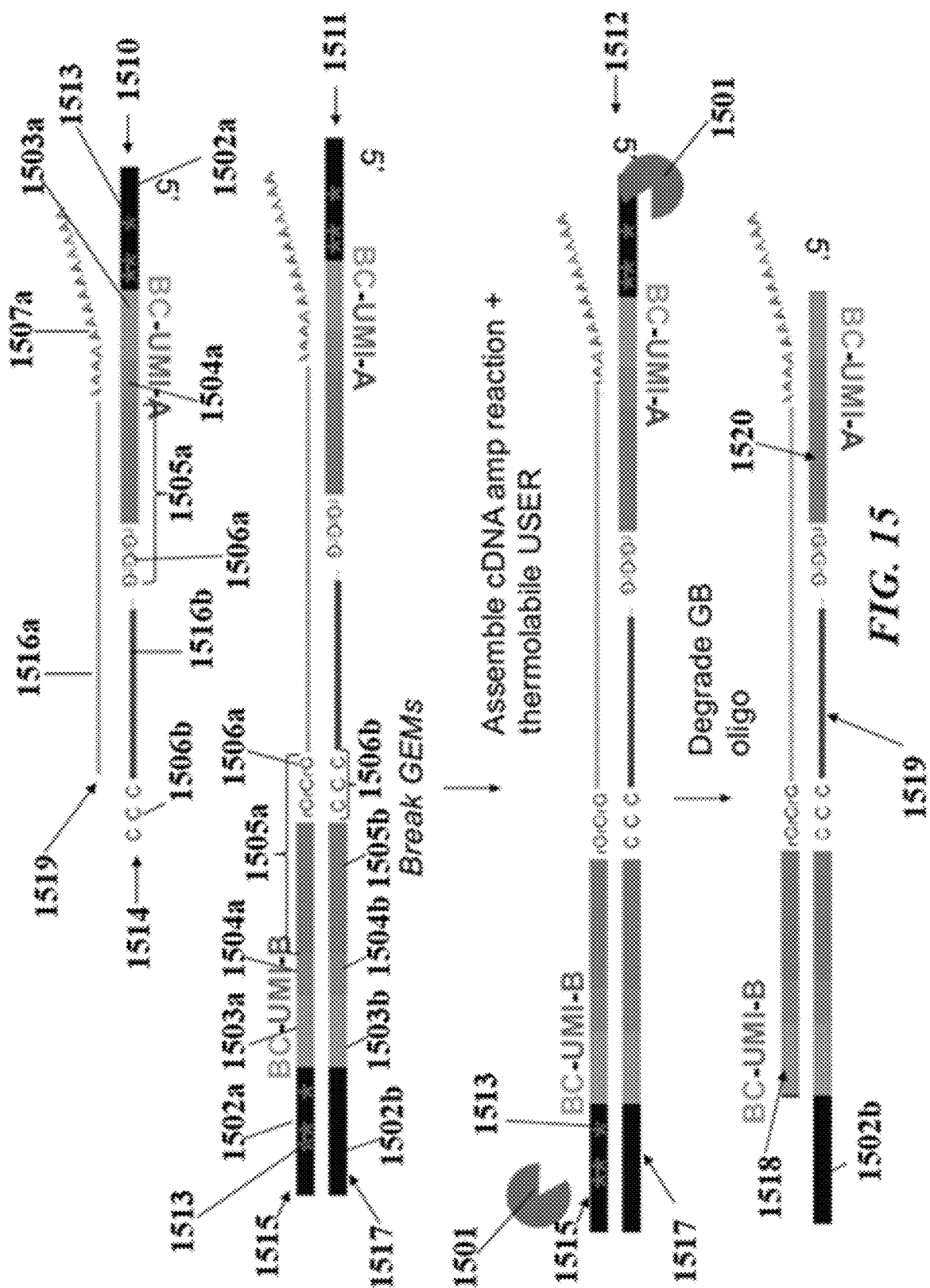
FIG. 15 illustrates the selective degradation of the handle sequence of the mis-primed extension product of FIG. 7.

FIG. 10 and FIG. 15 illustrate an example of an application of the claimed invention to prevent the production of the mis-primed extension product nucleic acid molecule 917 of FIG. 9 and reduce or prevent the production of the anti-sense cleavage product nucleic acid molecule 918 of FIG. 9. FIG. 10 illustrates an example of an application of the claimed invention in which the barcode nucleic acid strand 1015 can comprise one or more modified nucleotides 1013 that are configured to be cleaved by a cleaving agent 1001. In step 1010, a target mRNA nucleic acid molecule 1019 comprising a target sequence 1016a and a poly-A tail sequence 1007a, can be correctly reverse transcribed to produce a target DNA nucleic acid molecule 1014 comprising an amplification sequence 1007b, a poly-dT sequence 1007c, a DNA complement 1016b of the target sequence 1016a, and a complement of a template switching sequence 1006b. In step 1020, the target DNA nucleic acid molecule 1014 can be associated with a barcode nucleic acid strand via the template switching rGrGrG sequence 1006a of the barcode nucleic acid strand and an extension reaction can be performed to produce an extension product nucleic acid molecule 1017. The barcode nucleic acid strand can comprise a handle sequence 1002a, a barcode sequence 1003a, a unique molecular identifier 1004a, and/or a template switching sequence 1005a. The template switching sequence 1005a can comprise an rGrGrG sequence 1006a. The handle sequence 1002a can comprise one or more modified nucleotides 1013 that are configured to be cleaved by a cleaving agent 1001. The extension product 1017 comprises a complement of the handle sequence 1002b that does not comprise the one or more modified nucleotides 1013, a complement of the barcode sequences 1003b, a complement of the unique molecular identifier 1004b, a complement of the template switching sequence 1005b that comprises a CCC sequence 1006b, the target DNA sequence 1016b, the poly-dT sequence 1007c, and the amplification sequence 1007b. In step 1030, the cleaving agent 1001 can cleave the handle sequence 1002a. Second strand synthesis may then be performed to create a double-stranded cDNA product comprising the handle sequence 1002a without the modified nucleotides. In step 1040, the double-stranded cDNA product 1017 can be amplified using a first primer 1008 that can be complementary to 1002b and a second primer 1009 that can be complementary to the amplification sequence 1007b. The cleaved barcode nucleic acid strand 1018 is amplified as it comprises primer binding sites for the first primer 1008 and the second primer 1009.

FIG. 15 illustrates an example of an application of the claimed invention in which the barcode nucleic acid strand 1515 can comprise one or more modified nucleotide 1513 that are configured to be cleaved by a cleaving agent 1501. In step 1510, a target mRNA nucleic acid molecule 1519 can be mis-primed to a barcode nucleic acid strand and can be reverse transcribed to produce a mis-primed DNA nucleic acid molecule 1514. The target mRNA nucleic acid molecule 1519 can comprise a target sequence 1516 and a poly-A tail sequence 1507a. The mis-primed DNA nucleic acid molecule 1514 can comprise a whole or partial DNA complement of the target sequence 1516, a complement of a template switching sequence 1506b, a handle sequence 1502a, a barcode sequence 1503a, a unique molecular identifier 1504a, and/or a template switching sequence 1505a. In step 1511, the mis-primed DNA oligonucleotide 1514 can be associated with a barcode nucleic acid strand via the template switching rGrGrG sequence 1506a of the barcode nucleic acid strand and an extension reaction can be performed to produce an extension product 1517. The barcode nucleic acid strand can comprise a handle sequence 1502a, a barcode sequences 1503a, a unique molecular identifier 1504a, and/or a template switching sequence 1505a that comprises an rGrGrG sequence 1506a. The handle sequence 1502a comprises one or more modified nucleotides 1513 that are configured to be cleaved by a cleaving agent 1501. The extension product 1517 can comprise a complement of the handle sequence 1502b that does not comprise the modified nucleotide 1513, a complement of the barcode sequences 1503b, a complement of the unique molecular identifier 1504b, a complement of the template switching sequence 1505b that comprises a CCC sequence 1606b, the target DNA sequence 1516b, a handle sequence 1502a, a barcode sequences 1503a, a unique molecular identifier 1504a, and/or a template switching sequence 1505a that comprises a rGrGrG template switching sequence 1506a. In step 1512, the cleaving agent 1501 can cleave the handle sequence 1502a on both the barcode nucleic acid strand 1515 and the extension product 1517 to produce a cleaved extension product 1519. The cleaved extension product 1519 is not exponentially amplified since, while it contains a primer binding site for the first primer at one end, it has no primer binding site for either the first or second primer on the other end, as identified in FIG. 10.

The cleaving agent can be an enzyme, chemical reactant, light, a change in temperature, a change in pressure, or a change in ion concentration. The cleaving agent can be an N-glycosylase. The cleaving agent can be a uracil DNA glycosylase and/or an endonuclease VIII. The enzyme can be an AP-lyase. The enzyme can be endonuclease III, a uracil-DNA glycosylase (UDG), endonuclease VIII, Afu Uraci-DNA Glycosylase (UDG), antarctic thermolabile UDG, Tma endonuclease III, endonuclease IV, Tth endonuclease IV, endonuclease V, formamidopyrimidine DNA glycosylase (Fpg), human alkyl adenine DNA glycosylase (hAAG), hSMUG1, T4 PDG (T4 endonuclease V), hNEIL1, or hOGG1. The modified nucleotide can be deoxyuridine, 5,6-dihydroxythymine, thymine glycol, 5-hydroxy-5-methylhydantoin, uracil glycol, 6-hydroxy-5,6-dihydrothymine, deoxyuridine, 7,8-dihydro-8-oxoguanine (8-oxoguanine); 8-oxoadenine, fapy-guanine, methyl-fapy-guanine, fapyadenine, aflatoxin B1-fapy-guanine, 5-hydroxy-cytosine, 5-hydroxyuracil, 5-hydroxymethyluracil, 5-formyluracil, is-syn cyclobutene pyrimidine dimer(s), 5,6-dihydrothymine, 5,6-dihydroxyuracil, 4,6-diamino-5-formamidopyrimidine, or 2,6-diamino-4-hydroxy-5-formamidopyrimidine.

The modified nucleotide can comprise a photolabile linker.

In some aspects, the cleaving agent is provided with the target mRNA molecules, and reverse transcription reactants. In some aspects, the cleaving agent is provided subsequent to the reverse transcription reaction. In some aspects, the cleaving agent is deactivated by a change in reaction conditions. The reaction conditions can include ion concentration, pH, pressure, temperature, light, a deactivating agent, etc. The deactivating agent can be a chemical reagent. The deactivating agent can be a binding molecule. The deactivating agent can be a protein. In some aspects, the cleaving agent is an enzyme that is deactivated by a change in reaction conditions. In some aspects, the cleaving agent is an enzyme that is deactivated by a change in temperature. In some aspects, the cleaving agent is an enzyme that is deactivated by an increase in temperature prior to an amplification reaction. In some aspects the cleaving agent is an enzyme that is deactivated by an increase in temperature during an amplification reaction. In some aspects the cleaving agent is providing within a bead. In some aspects, the bead is ruptured to release the cleaving agent. The bead can be ruptured by any method described herein. The bead can be a gel bead as described herein.

Systems and Methods for Sample Compartmentalization

In an aspect, the systems and methods described herein provide for the compartmentalization, depositing, or partitioning of one or more particles (e.g., analyte carriers, macromolecular constituents of analyte carriers, beads, reagents, etc.) into discrete compartments or partitions (referred to interchangeably herein as partitions), where each partition maintains separation of its own contents from the contents of other partitions. The partition can be a droplet in an emulsion or a well. A partition may comprise one or more other partitions.

A partition may include one or more particles. A partition may include one or more types of particles. For example, a partition of the present disclosure may comprise one or more analyte carriers and/or macromolecular constituents thereof. A partition may comprise one or more beads. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be an analyte carrier and/or one or more of its macromolecular constituents encased inside of a gel or polymer matrix, such as via polymerization of a droplet containing the analyte carrier and precursors capable of being polymerized or gelled. Unique identifiers, such as barcodes, may be injected into the droplets previous to, subsequent to, or concurrently with droplet generation, such as via a microcapsule (e.g., bead), as described elsewhere herein.

The methods and systems of the present disclosure may comprise methods and systems for generating one or more partitions such as droplets. The droplets may comprise a plurality of droplets in an emulsion. In some examples, the droplets may comprise droplets in a colloid. In some cases, the emulsion may comprise a microemulsion or a nanoemulsion. In some examples, the droplets may be generated with aid of a microfluidic device and/or by subjecting a mixture of immiscible phases to agitation (e.g., in a container). In some cases, a combination of the mentioned methods may be used for droplet and/or emulsion formation.

Droplets can be formed by creating an emulsion by mixing and/or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

Microfluidic devices or platforms comprising microfluidic channel networks (e.g., on a chip) can be utilized to generate partitions such as droplets and/or emulsions as described herein. Methods and systems for generating partitions such as droplets, methods of encapsulating analyte carriers and/or analyte carriers in partitions, methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In some examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as analyte carriers or biological particles, in some cases, individual analyte carriers such as single cells. In some examples, reagents may be encapsulated and/or partitioned (e.g., co-partitioned with analyte carriers) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of analyte carriers per partition, number of beads per partition, etc.). For example, partition occupancy can be controlled by providing the aqueous stream at a certain concentration and/or flow rate of particles. To generate single analyte carrier partitions, the relative flow rates of the immiscible fluids can be selected such that, on average, the partitions may contain less than one analyte carrier per partition in order to ensure that those partitions that are occupied are primarily singly occupied. In some cases, partitions among a plurality of partitions may contain at most one analyte carrier (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual analyte carriers (also referred to herein as biological particles). The channel structure 100 can include channel segments 102, 104, 106 and 108 communicating at a channel junction 110. In operation, a first aqueous fluid 112 that includes suspended analyte carriers (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual analyte carrier 114 (such as droplets 118). A discrete droplet generated may include more than one individual analyte carrier 114 (not shown in FIG. 1). A discrete droplet may contain no analyte carrier 114 (such as droplet 120). Each discrete partition may maintain separation of its own contents (e.g., individual analyte carrier 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., analyte carriers, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more analyte carriers 114, and (2) unoccupied droplets 120, not containing any analyte carriers 114. Occupied droplets 118 may comprise singly occupied droplets (having one analyte carrier) and multiply occupied droplets (having more than one analyte carrier). As described elsewhere herein, in some cases, the majority of occupied partitions can include no more than one analyte carrier per occupied partition and some of the generated partitions can be unoccupied (of any analyte carrier). In some cases, though, some of the occupied partitions may include more than one analyte carrier. In some cases, the partitioning process may be controlled such that fewer than about 25% of the occupied partitions contain more than one analyte carrier, and in many cases, fewer than about 20% of the occupied partitions have more than one analyte carrier, while in some cases, fewer than about 10% or even fewer than about 5% of the occupied partitions include more than one analyte carrier per partition.

In some cases, it may be desirable to minimize the creation of excessive numbers of empty partitions, such as to reduce costs and/or increase efficiency. While this minimization may be achieved by providing a sufficient number of analyte carriers (e.g., analyte carriers 114) at the partitioning junction 110, such as to ensure that at least one analyte carrier is encapsulated in a partition, the Poissonian distribution may expectedly increase the number of partitions that include multiple analyte carriers. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the analyte carriers (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

As will be appreciated, the above-described occupancy rates are also applicable to partitions that include both analyte carriers and additional reagents, such as microcapsules or beads (e.g., gel beads) carrying barcoded nucleic acid molecules (e.g., oligonucleotides). In some cases, the occupied partitions (e.g., at least about 10%, 20%, 30%, 40%, 50%, 60%, 70%, 80%, 90%, 95%, or 99% of the occupied partitions) may comprise both a microcapsule (e.g., bead) comprising barcoded nucleic acid molecules and an analyte carrier.

Figure 17:
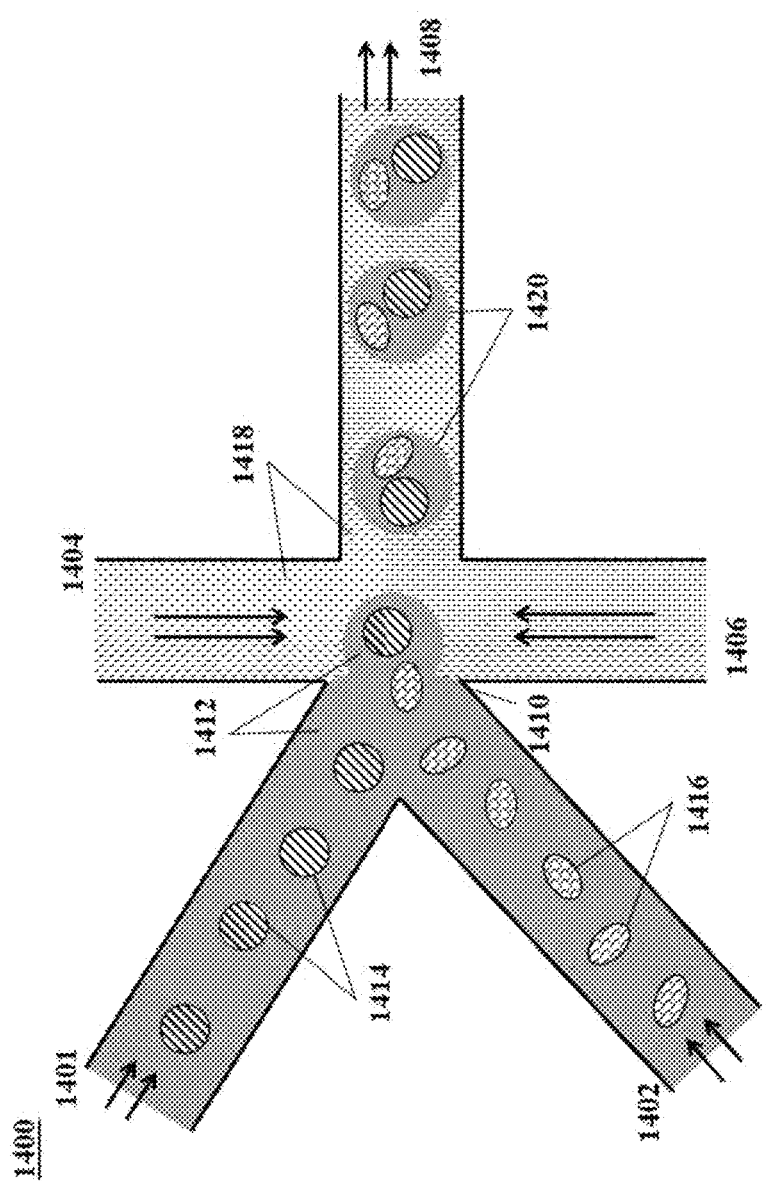
FIG. 17 shows an exemplary microfluidic channel structure for delivering barcode carrying beads to droplets.

FIG. 17 shows an example of a microfluidic channel structure 1400 for delivering barcode carrying beads to droplets. The channel structure 1400 can include channel segments 1401, 1402, 1404, 1406 and 1408 communicating at a channel junction 1410. In operation, the channel segment 1401 may transport an aqueous fluid 1412 that includes a plurality of beads 1414 (e.g., with nucleic acid molecules, e.g., nucleic acid barcode molecules or barcoded oligonucleotides, molecular tags) along the channel segment 1401 into junction 1410. The plurality of beads 1414 may be sourced from a suspension of beads. For example, the channel segment 1401 may be connected to a reservoir comprising an aqueous suspension of beads 1414. The channel segment 1402 may transport the aqueous fluid 1412 that includes a plurality of biological particles 1416 along the channel segment 1402 into junction 1410. The plurality of biological particles 1416 may be sourced from a suspension of biological particles. For example, the channel segment 1402 may be connected to a reservoir comprising an aqueous suspension of biological particles 1416. In some instances, the aqueous fluid 1412 in either the first channel segment 1401 or the second channel segment 1402, or in both segments, can include one or more reagents, as further described below. A second fluid 1418 that is immiscible with the aqueous fluid 1412 (e.g., oil) can be delivered to the junction 1410 from each of channel segments 1404 and 1406. Upon meeting of the aqueous fluid 1412 from each of channel segments 1401 and 1402 and the second fluid 1418 from each of channel segments 1404 and 1406 at the channel junction 1410, the aqueous fluid 1412 can be partitioned as discrete droplets 1420 in the second fluid 1418 and flow away from the junction 1410 along channel segment 1408. The channel segment 1408 may deliver the discrete droplets to an outlet reservoir fluidly coupled to the channel segment 1408, where they may be harvested. As an alternative, the channel segments 1401 and 1402 may meet at another junction upstream of the junction 1410. At such junction, beads and biological particles may form a mixture that is directed along another channel to the junction 1410 to yield droplets 1420. The mixture may provide the beads and biological particles in an alternating fashion, such that, for example, a droplet comprises a single bead and a single biological particle.

In another aspect, in addition to or as an alternative to droplet-based partitioning, analyte carriers (e.g., biological particles) may be comprised within (e.g., encapsulated within) a microcapsule that comprises an outer shell, layer or porous matrix in which is entrained one or more individual analyte carriers or small groups of analyte carriers. The microcapsule may include other reagents. Encapsulation of analyte carriers may be performed by a variety of processes. Such processes may combine an aqueous fluid containing the analyte carriers with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of microcapsules comprising analyte carriers may be performed by a variety of methods. For example, air knife droplet or aerosol generators may be used to dispense droplets of precursor fluids into gelling solutions in order to form microcapsules that include individual analyte carriers or small groups of analyte carriers. Likewise, membrane-based encapsulation systems may be used to generate microcapsules comprising encapsulated analyte carriers as described herein. Microfluidic systems of the present disclosure, such as that shown in FIG. 1, may be readily used in encapsulating cells as described herein. In particular, and with reference to FIG. 1, the aqueous fluid 112 comprising (i) the analyte carriers 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained analyte carriers. Examples of polymer precursor/initiator pairs include those described in U.S. Patent Application Publication No. 2014/0378345, which is entirely incorporated herein by reference for all purposes. For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature-based gelling (e.g., upon cooling, etc.).

In some cases, encapsulated analyte carriers can be selectively releasable from the microcapsule, such as through passage of time or upon application of a particular stimulus, that degrades the microcapsule sufficiently to allow the analyte carriers (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The analyte carrier can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the analyte carrier. The polymer or gel may be diffusively permeable to chemical or biochemical reagents. The polymer or gel may be diffusively impermeable to macromolecular constituents of the analyte carrier. In this manner, the polymer or gel may act to allow the analyte carrier to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the analyte carrier may be surrounded by polyacrylamide strands linked together by disulfide bridges. In this manner, the analyte carrier may be encased inside of or comprise a gel or matrix (e.g., polymer matrix) to form a "cell bead."

A cell bead can contain analyte carriers (e.g., a cell) or macromolecular constituents (e.g., RNA, DNA, proteins, etc.) of analyte carriers. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing analyte carriers and cell beads (and/or droplets or other partitions) containing macromolecular constituents of analyte carriers. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Encapsulated analyte carriers and/or analyte carriers can provide certain potential advantages of being more storable and more portable than droplet-based partitioned analyte carriers and/or analyte carriers. Furthermore, in some cases, it may be desirable to allow analyte carriers to incubate for a select period of time before analysis, such as in order to characterize changes in such analyte carriers over time, either in the presence or absence of different stimuli (or reagents). In such cases, encapsulation may allow for longer incubation than partitioning in emulsion droplets, although in some cases, droplet partitioned analyte carriers may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of analyte carriers may constitute the partitioning of the analyte carriers into which other reagents are co-partitioned. Alternatively or in addition, encapsulated analyte carriers may be readily deposited into other partitions (e.g., droplets) as described above.

Wells

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (µL), at most 100 µL, at most 10 µL, at most 1 µL, at most 100 nanoliters (nL), at most 10 nL, at most 1 nL, at most 100 picoliters (µL), at most 10 (µL), or less. The well may be configured to hold a volume of about 1000 µL, about 100 µL, about 10 µL, about 1 µL, about 100 nL, about 10 nL, about 1 nL, about 100 µL, about 10 µL, etc. The well may be configured to hold a volume of at least 10 µL, at least 100 µL, at least 1 nL, at least 10 nL, at least 100 nL, at least 1 µL, at least 10 µL, at least 100 µL, at least 1000 µL, or more. The well may be configured to hold a volume in a range of volumes listed herein, for example, from about 5 nL to about 20 nL, from about 1 nL to about 100 nL, from about 500 µL to about 100 µL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a microcapsule, droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a microcapsule or bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the microcapsule or bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

A well may comprise free reagents and/or reagents encapsulated in, or otherwise coupled to or associated with, microcapsules, beads, or droplets. Any of the reagents described in this disclosure may be encapsulated in, or otherwise coupled to, a microcapsule, droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a microcapsule, bead, or droplet that comprises a set of reagents that has a similar attribute (e.g., a set of enzymes, a set of minerals, a set of oligonucleotides, a mixture of different barcode molecules, a mixture of identical barcode molecules). In other cases, a microcapsule, bead, or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different microcapsule, droplet, or bead, or within a solution within a partition (e.g., microwell) of the system.

Figure 5:
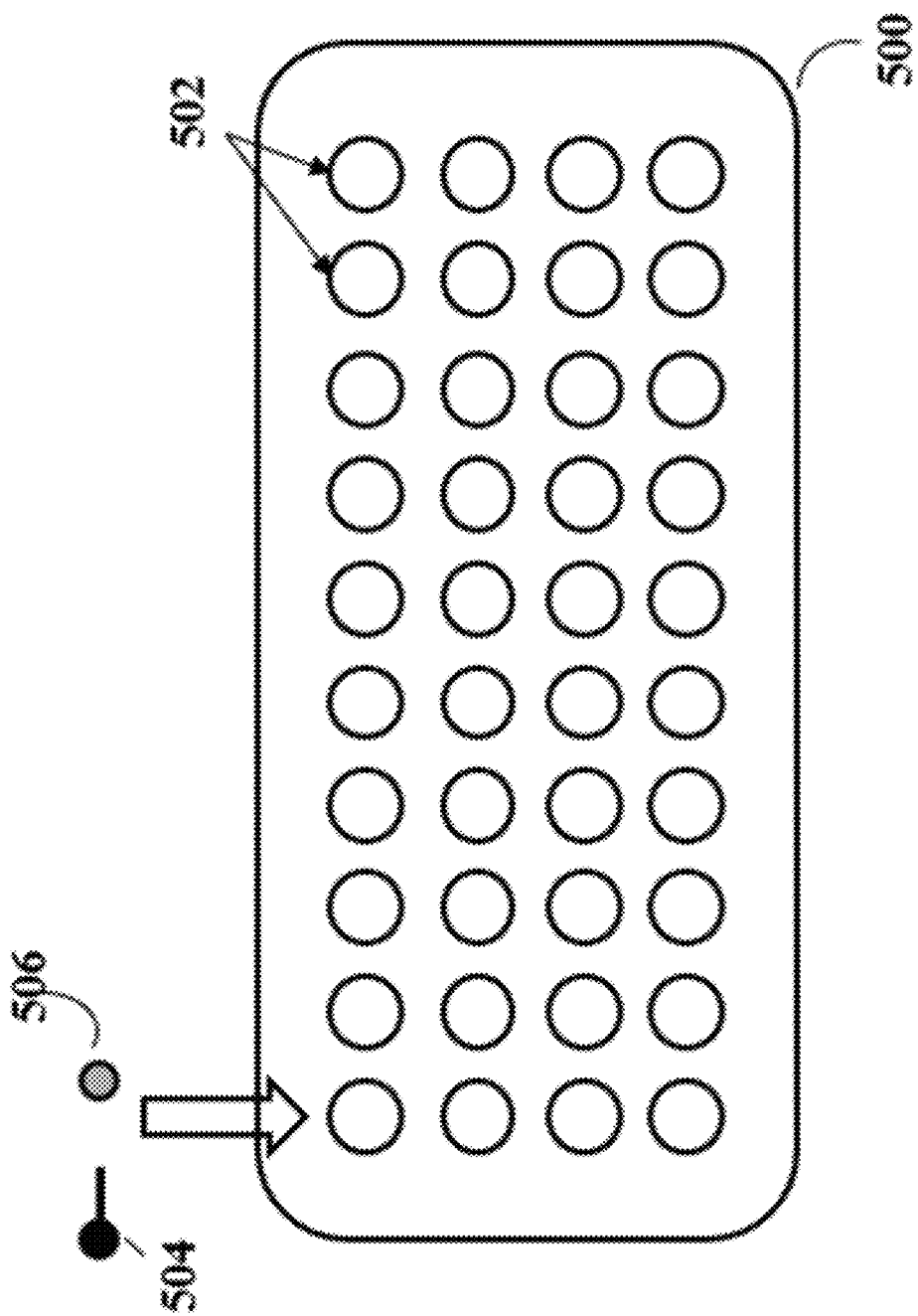
FIG. 5 schematically illustrates an example microwell array.

FIG. 5 schematically illustrates an example of a microwell array. The array can be contained within a substrate 500. The substrate 500 comprises a plurality of wells 502. The wells 502 may be of any size or shape, and the spacing between the wells, the number of wells per substrate, as well as the density of the wells on the substrate 500 can be modified, depending on the particular application. In one such example application, a sample molecule 506, which may comprise a cell or cellular components (e.g., nucleic acid molecules) is co-partitioned with a bead 504, which may comprise a nucleic acid barcode molecule coupled thereto. The wells 502 may be loaded using gravity or other loading technique (e.g., centrifugation, liquid handler, acoustic loading, optoelectronic, etc.). In some instances, at least one of the wells 502 contains a single sample molecule 506 (e.g., cell) and a single bead 504.

Reagents may be loaded into a well either sequentially or concurrently. In some cases, reagents are introduced to the device either before or after a particular operation. In some cases, reagents (which may be provided, in certain instances, in microcapsules, droplets, or beads) are introduced sequentially such that different reactions or operations occur at different steps. The reagents (or microcapsules, droplets, or beads) may also be loaded at operations interspersed with a reaction or operation step. For example, microcapsules (or droplets or beads) comprising reagents for fragmenting polynucleotides (e.g., restriction enzymes) and/or other enzymes (e.g., transposases, ligases, polymerases, etc.) may be loaded into the well or plurality of wells, followed by loading of microcapsules, droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a microcapsule, bead, or droplet. These microcapsules, beads, or droplets may be loaded into a partition (e.g., a microwell) before, after, or concurrently with the loading of a cell, such that each cell is contacted with a different microcapsule, bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet, bead, or microcapsule may be partitioned into a well. The droplets, microcapsules, or beads may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). The nucleic acid barcode molecules may be attached to a droplet or bead that has been partitioned into the well. In some instances, the nucleic acid barcode molecules may be releasable from the bead or droplet. In some instances nucleic acid barcode molecules attached to a bead in a well may be hybridized to sample nucleic acid molecules, and the bead with the sample nucleic acid molecules hybridized thereto may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 6:
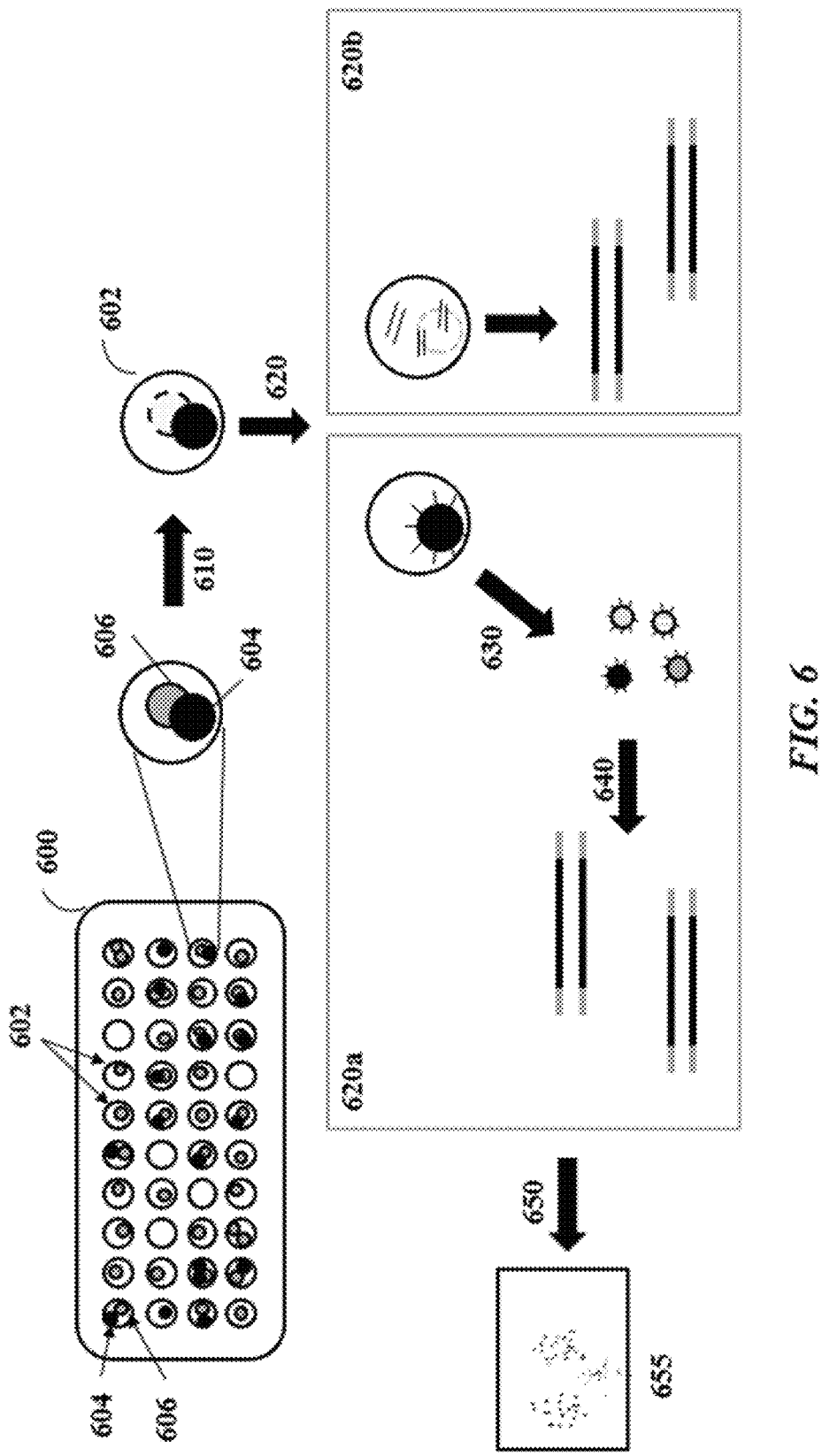
FIG. 6 schematically illustrates an example workflow for processing nucleic acid molecules.

FIG. 6 schematically shows an example workflow for processing nucleic acid molecules within a sample. A substrate 600 comprising a plurality of microwells 602 may be provided. A sample 606 which may comprise a cell, cell bead, cellular components or analytes (e.g., proteins and/or nucleic acid molecules) can be co-partitioned, in a plurality of microwells 602, with a plurality of beads 604 comprising nucleic acid barcode molecules. During process 610, the sample 606 may be processed within the partition. For instance, in the case of live cells, the cell may be subjected to conditions sufficient to lyse the cells and release the analytes contained therein. In process 620, the bead 604 may be further processed. By way of example, processes 620a and 620b schematically illustrate different workflows, depending on the properties of the bead 604.

In 620a, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 630, the beads 604 from multiple wells 602 may be collected and pooled. Further processing may be performed in process 640. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

In 620b, the bead comprises nucleic acid barcode molecules that are releasably attached thereto, as described below. The bead may degrade or otherwise release the nucleic acid barcode molecules into the well 602; the nucleic acid barcode molecules may then be used to barcode nucleic acid molecules within the well 602. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

Beads

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be at least partially dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned analyte carrier. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual analyte carrier to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the bead (e.g., microcapsule) and then released from the bead. Release of the barcoded nucleic acid molecules can be passive (e.g., by diffusion out of the bead). In addition or alternatively, release from the bead can be upon application of a stimulus which allows the barcoded nucleic acid nucleic acid molecules to dissociate or to be released from the bead. Such stimulus may disrupt the bead, an interaction that couples the barcoded nucleic acid molecules to or within the bead, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof. Methods and systems for partitioning barcode carrying beads into droplets are provided in US. Patent Publication Nos. 2019/0367997 and 2019/0064173, and International Application No. PCT/US20/17785, each of which is herein entirely incorporated by reference for all purposes.

In some examples, beads, analyte carriers, and droplets may flow along channels (e.g., the channels of a microfluidic device), in some cases at substantially regular flow profiles (e.g., at regular flow rates). Such regular flow profiles may permit a droplet to include a single bead and a single analyte carrier. Such regular flow profiles may permit the droplets to have an occupancy (e.g., droplets having beads and analyte carriers) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible crosslinking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a target nucleic acid sequence and/or for amplifying a target nucleic acid sequence, a random primer, or a primer sequence for messenger RNA) that is useful for incorporation into the bead, etc.) and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence (or a portion thereof) for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise a barcode sequence. In some cases, the nucleic acid molecule can further comprise a unique molecular identifier (UMI). In some cases, the nucleic acid molecule can comprise an R1 primer sequence for Illumina sequencing. In some cases, the nucleic acid molecule can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In some cases, the nucleic acid molecule can comprise one or more functional sequences. For example, a functional sequence can comprise a sequence for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the functional sequence can comprise a barcode sequence or multiple barcode sequences. In some cases, the functional sequence can comprise a unique molecular identifier (UMI). In some cases, the functional sequence can comprise a primer sequence (e.g., an R1 primer sequence for Illumina sequencing, an R2 primer sequence for Illumina sequencing, etc.). In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof.

Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 3:
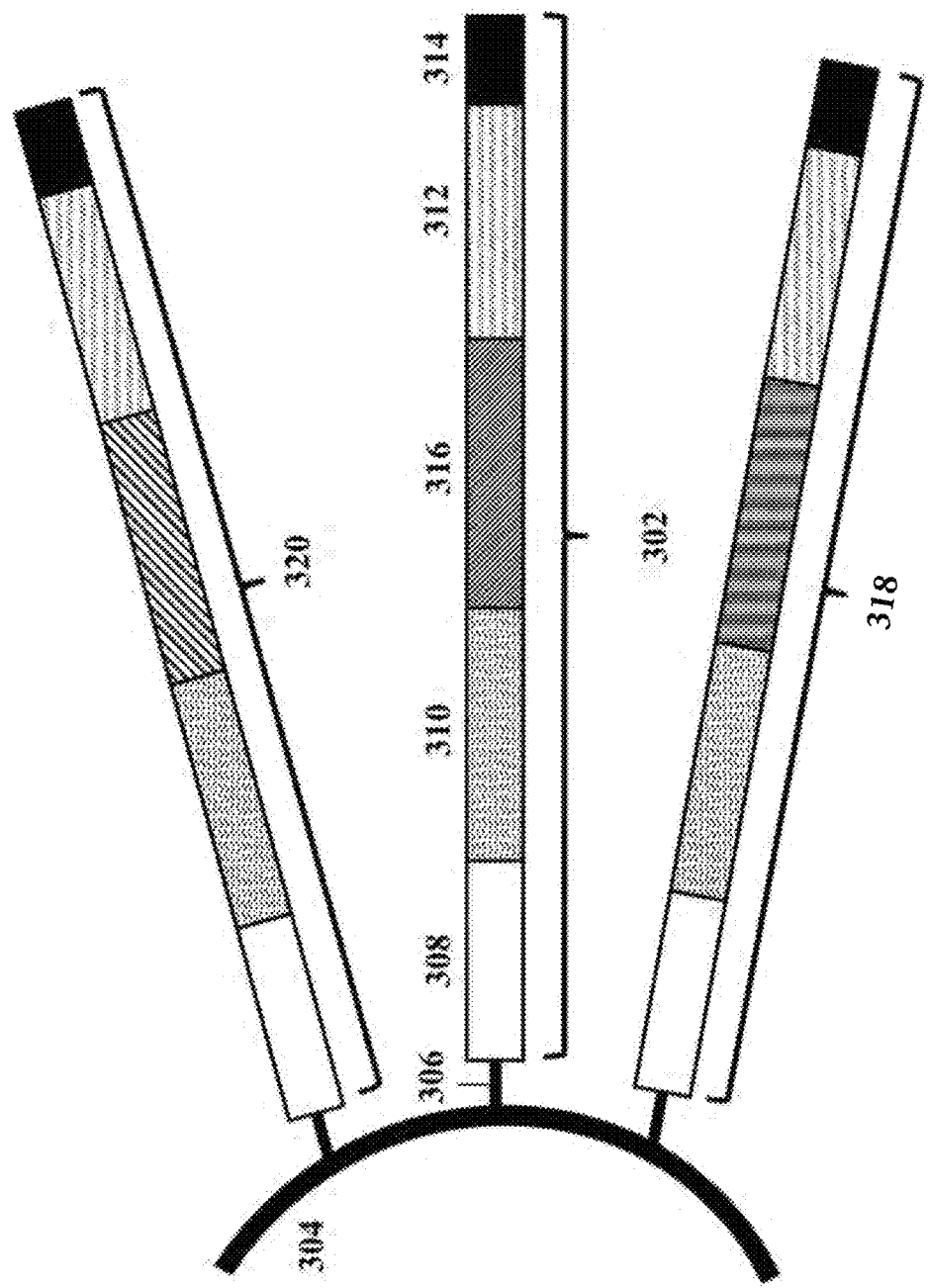
FIG. 3 illustrates an example of a barcode carrying bead.

FIG. 3 illustrates an example of a barcode carrying bead. A nucleic acid molecule 302, such as an oligonucleotide, can be coupled to a bead 304 by a releasable linkage 306, such as, for example, a disulfide linker. The same bead 304 may be coupled (e.g., via releasable linkage) to one or more other nucleic acid molecules 318, 320. The nucleic acid molecule 302 may be or comprise a barcode. As noted elsewhere herein, the structure of the barcode may comprise a number of sequence elements. The nucleic acid molecule 302 may comprise a functional sequence 308 that may be used in subsequent processing. For example, the functional sequence 308 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid molecule 302 may comprise a barcode sequence 310 for use in barcoding the sample (e.g., DNA, RNA, protein, etc.). In some cases, the barcode sequence 310 can be bead-specific such that the barcode sequence 310 is common to all nucleic acid molecules (e.g., including nucleic acid molecule 302) coupled to the same bead 304. Alternatively or in addition, the barcode sequence 310 can be partition-specific such that the barcode sequence 310 is common to all nucleic acid molecules coupled to one or more beads that are partitioned into the same partition. The nucleic acid molecule 302 may comprise a specific priming sequence 312, such as an mRNA specific priming sequence (e.g., poly-T sequence), a targeted priming sequence, and/or a random priming sequence. The nucleic acid molecule 302 may comprise an anchoring sequence 314 to ensure that the specific priming sequence 312 hybridizes at the sequence end (e.g., of the mRNA). For example, the anchoring sequence 314 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 302 may comprise a unique molecular identifying sequence 316 (e.g., unique molecular identifier (UMI)). In some cases, the unique molecular identifying sequence 316 may comprise from about 5 to about 8 nucleotides. Alternatively, the unique molecular identifying sequence 316 may compress less than about 5 or more than about 8 nucleotides. The unique molecular identifying sequence 316 may be a unique sequence that varies across individual nucleic acid molecules (e.g., 302, 318, 320, etc.) coupled to a single bead (e.g., bead 304). In some cases, the unique molecular identifying sequence 316 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 3 shows three nucleic acid molecules 302, 318, 320 coupled to the surface of the bead 304, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 308, 310, 312, etc.) and variable or unique sequence segments (e.g., 316) between different individual nucleic acid molecules coupled to the same bead.

In operation, an analyte carrier (e.g., cell, DNA, RNA, etc.) can be co-partitioned along with a barcode bearing bead 304. The nucleic acid barcode molecules 302, 318, 320 can be released from the bead 304 in the partition. By way of example, in the context of analyzing sample RNA, the poly-T segment (e.g., 312) of one of the released nucleic acid molecules (e.g., 302) can hybridize to the poly-A tail of a mRNA molecule. Reverse transcription may result in a cDNA transcript of the mRNA, but which transcript includes each of the sequence segments 308, 310, 316 of the nucleic acid molecule 302. Because the nucleic acid molecule 302 comprises an anchoring sequence 314, it will more likely hybridize to and prime reverse transcription at the sequence end of the poly-A tail of the mRNA. Within any given partition, all of the cDNA transcripts of the individual mRNA molecules may include a common barcode sequence segment 310. However, the transcripts made from the different mRNA molecules within a given partition may vary at the unique molecular identifying sequence 312 segment (e.g., UMI segment). Beneficially, even following any subsequent amplification of the contents of a given partition, the number of different UMIs can be indicative of the quantity of mRNA originating from a given partition, and thus from the analyte carrier (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, an analyte carrier (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 4:
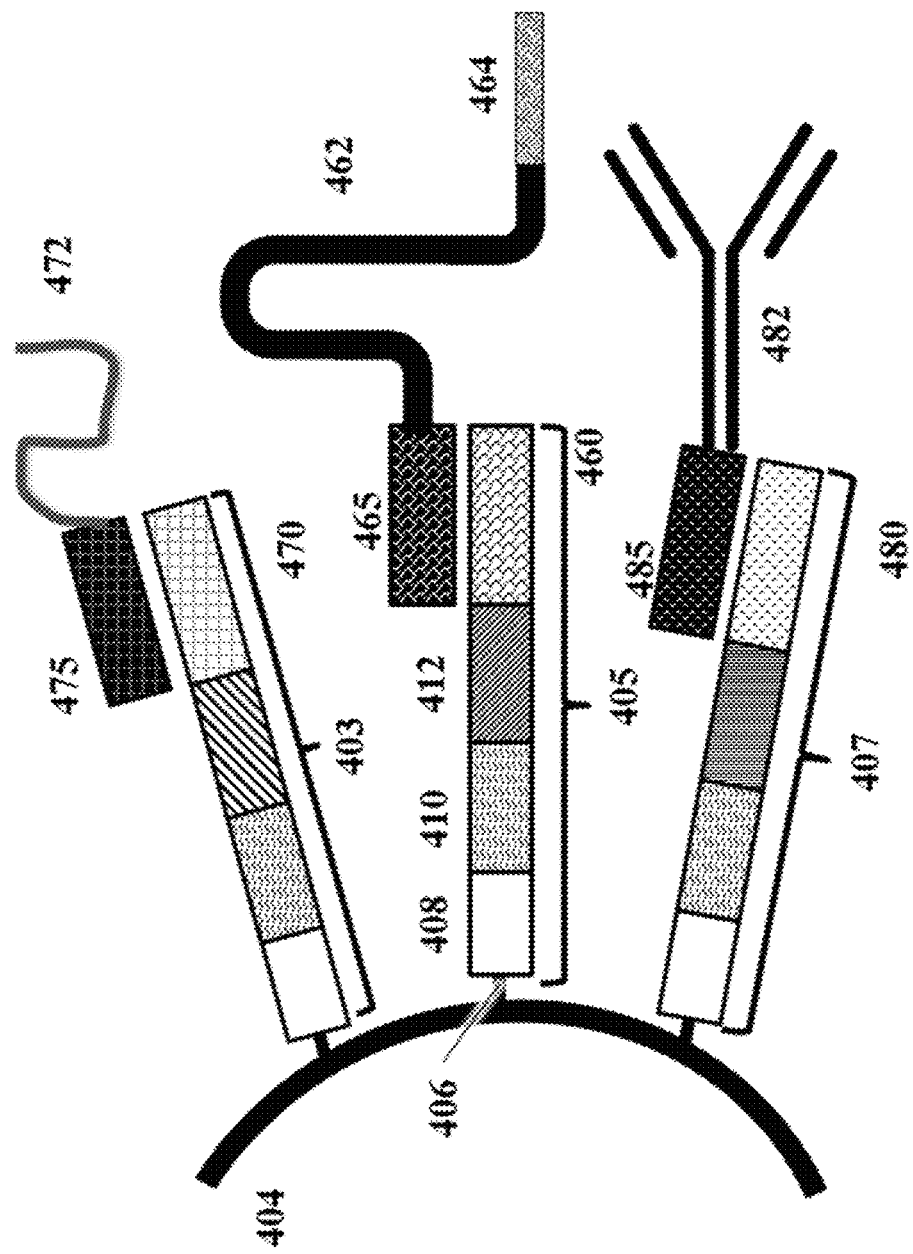
FIG. 4 illustrates another example of a barcode carrying bead.

FIG. 4 illustrates another example of a barcode carrying bead. A nucleic acid molecule 405, such as an oligonucleotide, can be coupled to a bead 404 by a releasable linkage 406, such as, for example, a disulfide linker. The nucleic acid molecule 405 may comprise a first capture sequence 460. The same bead 404 may be coupled (e.g., via releasable linkage) to one or more other nucleic acid molecules 403, 407 comprising other capture sequences. The nucleic acid molecule 405 may be or comprise a barcode. As noted elsewhere herein, the structure of the barcode may comprise a number of sequence elements, such as a functional sequence 408 (e.g., flow cell attachment sequence, sequencing primer sequence, etc.), a barcode sequence 410 (e.g., bead-specific sequence common to bead, partition-specific sequence common to partition, etc.), and a unique molecular identifier 412 (e.g., unique sequence within different molecules attached to the bead), or partial sequences thereof. The capture sequence 460 may be configured to attach to a corresponding capture sequence 465. In some instances, the corresponding capture sequence 465 may be coupled to another molecule that may be an analyte or an intermediary carrier. For example, as illustrated in FIG. 4, the corresponding capture sequence 465 is coupled to a guide RNA molecule 462 comprising a target sequence 464, wherein the target sequence 464 is configured to attach to the analyte. Another oligonucleotide molecule 407 attached to the bead 404 comprises a second capture sequence 480 which is configured to attach to a second corresponding capture sequence 485. As illustrated in FIG. 4, the second corresponding capture sequence 485 is coupled to an antibody 482. In some cases, the antibody 482 may have binding specificity to an analyte (e.g., surface protein). Alternatively, the antibody 482 may not have binding specificity. Another oligonucleotide molecule 403 attached to the bead 404 comprises a third capture sequence 470 which is configured to attach to a second corresponding capture sequence 475. As illustrated in FIG. 4, the third corresponding capture sequence 475 is coupled to a molecule 472. The molecule 472 may or may not be configured to target an analyte. The other oligonucleotide molecules 403, 407 may comprise the other sequences (e.g., functional sequence, barcode sequence, UMI, etc.) described with respect to oligonucleotide molecule 405. While a single oligonucleotide molecule comprising each capture sequence is illustrated in FIG. 4, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 404 may comprise other capture sequences. Alternatively or in addition, the bead 404 may comprise fewer types of capture sequences (e.g., two capture sequences). Alternatively or in addition, the bead 404 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods.

Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. Oligonucleotide molecules comprising barcodes attached to a solid support can be referred to as barcode nucleic acid strands. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may comprise pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

In some examples, a partition of the plurality of partitions may comprise a single biological particle or analyte carrier (e.g., a single cell or a single nucleus of a cell). In some examples, a partition of the plurality of partitions may comprise multiple biological particles or analyte carriers. Such partitions may be referred to as multiply occupied partitions, and may comprise, for example, two, three, four or more cells and/or microcapsules (e.g., beads) comprising barcoded nucleic acid molecules (e.g., oligonucleotides) within a single partition. Accordingly, as noted above, the flow characteristics of the analyte carrier and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional beads (e.g., microcapsules) can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of beads (e.g., microcapsules) from each source, while ensuring a given pairing or combination of such beads into a partition with a given number of analyte carriers (e.g., one analyte carrier and one bead per partition).

The partitions described herein may comprise small volumes, for example, less than about 10 microliters (µL), 5 µL, 1 µL, 900 picoliters (µL), 800 µL, 700 µL, 600 µL, 500 µL, 400 µL, 300 µL, 200 µL, 100 µL, 50 µL, 20 µL, 10 µL, 1 µL, 500 nanoliters (nL), 100 nL, 50 nL, or less.

For example, in the case of droplet based partitions, the droplets may have overall volumes that are less than about 1000 µL, 900 µL, 800 µL, 700 µL, 600 µL, 500 µL, 400 µL, 300 µL, 200 µL, 100 µL, 50 µL, 20 µL, 10 µL, 1 µL, or less.

Where co-partitioned with beads or microcapsules, it will be appreciated that the sample fluid volume, e.g., including co-partitioned analyte carriers and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Flow Sorting

A sample may derive from any useful source including any subject, such as a human subject. A sample may comprise material (e.g., one or more analyte carriers) from one or more different sources, such as one or more different subjects. Multiple samples, such as multiple samples from a single subject (e.g., multiple samples obtained in the same or different manners from the same or different bodily locations, and/or obtained at the same or different times (e.g., seconds, minutes, hours, days, weeks, months, or years apparat)), or multiple samples from different subjects, may be obtained for analysis as described herein. For example, a first sample may be obtained from a subject at a first time and a second sample may be obtained from the subject at a second time later than the first time. The first time may be before a subject undergoes a treatment regimen or procedure (e.g., to address a disease or condition), and the second time may be during or after the subject undergoes the treatment regimen or procedure. In another example, a first sample may be obtained from a first bodily location or system of a subject (e.g., using a first collection technique) and a second sample may be obtained from a second bodily location or system of the subject (e.g., using a second collection technique), which second bodily location or system may be different than the first bodily location or system. In another example, multiple samples may be obtained from a subject at a same time from the same or different bodily locations. Different samples, such as different subjects collected from different bodily locations of a same subject, at different times, from multiple different subjects, and/or using different collection techniques, may undergo the same or different processing (e.g., as described herein). For example, a first sample may undergo a first processing protocol and a second sample may undergo a second processing protocol.

A sample may be a biological sample, such as a cell sample (e.g., as described herein). A sample may include one or more analyte carriers, such as one or more cells and/or cellular constituents, such as one or more cell nuclei. For example, a sample may comprise a plurality of analyte carriers, such as a plurality of cells and/or cellular constituents. Analyte carriers (e.g., cells or cellular constituents, such as cell nuclei) of a sample may be of a single type or a plurality of different types. For example, cells of a sample may include one or more different types or blood cells.

Cells and cellular constituents of a sample may be of any type. For example, a cell or cellular constituent may be a mammalian, fungal, plant, bacterial, or other cell type. In some cases, the cell is a mammalian cell, such as a human cell. The cell may be, for example, a stem cell, liver cell, nerve cell, bone cell, blood cell, reproductive cell, skin cell, skeletal muscle cell, cardiac muscle cell, smooth muscle cell, hair cell, hormone-secreting cell, or glandular cell. The cell may be, for example, an erythrocyte (e.g., red blood cell), a megakaryocyte (e.g., platelet precursor), a monocyte (e.g., white blood cell), a leukocyte, a B cell, a T cell (such as a helper, suppressor, cytotoxic, or natural killer T cell), an osteoclast, a dendritic cell, a connective tissue macrophage, an epidermal Langerhans cell, a microglial cell, a granulocyte, a hybridoma cell, a mast cell, a natural killer cell, a reticulocyte, a hematopoietic stem cell, a myoepithelial cell, a myeloid-derived suppressor cell, a platelet, a thymocyte, a satellite cell, an epithelial cell, an endothelial cell, an epididymal cell, a kidney cell, a liver cell, an adipocyte, a lipocyte, or a neuron cell. In some cases, the cell may be associated with a cancer, tumor, or neoplasm. In some cases, the cell may be associated with a fetus. In some cases, the cell may be a Jurkat cell.

A cell of a biological sample may have any feature or dimension. For example, a cell may have a first dimension, a second dimension, and a third dimension, where the first, second, and third dimensions are approximately the same. In other cases, the first and second dimensions may be approximately the same, and the third dimension may be different, or the first, second, and third dimensions may all be different. In some cases, a cell may comprise a dimension (e.g., a diameter) of at least about 1 µm. For example, a cell may comprise a dimension of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some cases, the cell may comprise a dimension of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, a cell may comprise a dimension of between about 1 µm and 100 µm. Any or all dimensions of a cell may be variable. For example, the dimensions of a substantially fluid cell may vary over a rapid timescale. Dimensions of a more rigid cell may be fixed or may vary with lesser amplitude. Accordingly, the dimensions provided herein may represent averages rather than fixed values. The volume of a cell may be at least about 1 µm$^3$. In some cases, the volume of a cell may be at least about 10 µm$^3$. For example, the volume of the cell may be at least 1 µm$^3$, 2 µm$^3$, 3 µm$^3$, 4 µm$^3$, 5 µm$^3$, 6 µm$^3$, 7 µm$^3$, 8 µm$^3$, 9 µm$^3$, 10 µm$^3$, 12 µm$^3$, 14 µm$^3$, 16 µm$^3$, 18 µm$^3$, 20 µm$^3$, 25 µm$^3$, 30 µm$^3$, 35 µm$^3$, 40 µm$^3$, 45 µm$^3$, 50 µm$^3$, 55 µm$^3$, 60 µm$^3$, 65 µm$^3$, 70 µm$^3$, 75 µm$^3$, 80 µm$^3$, 85 µm$^3$, 90 µm$^3$, 95 µm$^3$, 100 µm$^3$, 125 µm$^3$, 150 µm$^3$, 175 µm$^3$, 200 µm$^3$, 250 µm$^3$, 300 µm$^3$, 350 µm$^3$, 400 µm$^3$, 450 µm$^3$, µm$^3$, 500 µm$^3$, 550 µm$^3$, 600 µm$^3$, 650 µm$^3$, 700 µm$^3$, 750 µm$^3$, 800 µm$^3$, 850 µm$^3$, 900 µm$^3$, 950 µm$^3$, 1000 µm$^3$, 1200 µm$^3$, 1400 µm$^3$, 1600 µm$^3$, 1800 µm$^3$, 2000 µm$^3$, 2200 µm$^3$, 2400 µm$^3$, 2600 µm$^3$, 2800 µm$^3$, 3000 µm$^3$, or greater. In some cases, a cell may comprise a volume of between about 1 µm$^3$ and 100 µm$^3$, such as between about 1 µm$^3$ and 10 µm$^3$, between about 10 µm$^3$ and 50 µm$^3$, or between about 50 µm$^3$ and 100 µm$^3$. In some cases, a cell may comprise a volume of between about 100 µm$^3$ and 1000 µm$^3$, such as between about 100 µm$^3$ and 500 µm$^3$ or between about 500 µm$^3$ and 1000 µm$^3$. In some cases, a cell may comprise a volume between about 1000 µm$^3$ and 3000 µm$^3$, such as between about 1000 µm$^3$ and 2000 µm$^3$ or between about 2000 µm$^3$ and 3000 µm$^3$. In some cases, a cell may comprise a volume between about 1 µm$^3$ and 3000 µm$^3$, such as between about 1 µm$^3$ and 2000 µm$^3$, between about 1 µm$^3$ and 1000 µm$^3$, between about 1 µm$^3$ and 500 µm$^3$, or between about 1 µm$^3$ and 250 µm$^3$.

A cell of a biological sample may comprise one or more cross-sections that may be the same or different. In some cases, a cell may have a first cross-section that is different from a second cross-section. a cell may have a first cross-section that is at least about 1 µm. For example, a cell may comprise a cross-section (e.g., a first cross-section) of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some cases, a cell may comprise a cross-section (e.g., a first cross-section) of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, a cell may comprise a cross-section (e.g., a first cross-section) of between about 1 µm and 100 µm. In some cases, the cell may have a second cross-section that is at least about 1 µm. For example, the cell may comprise a second cross-section of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some cases, a cell may comprise a second cross-section of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, a cell may comprise a second cross-section of between about 1 µm and 100 µm.

A cross section (e.g., a first cross-section) may correspond to a diameter of a cell. In some cases, a cell may be approximately spherical. In such cases, the first cross-section may correspond to the diameter of the cell. In other cases, the cell may be approximately cylindrical. In such cases, the first cross-section may correspond to a diameter, length, or width along the approximately cylindrical cell. In some cases, the cell may comprise a surface. A cell surface may comprise one or more features. For example, a cell may comprise a dendritic receiver, flagella, roughed border, or other feature.

A characteristic or set of characteristics of a cell may be changed by one or more conditions. A condition suitable for changing a characteristic or set of characteristics of a cell may be, for example, a temperature, a pH, an ion or salt concentration, a pressure, or another condition. For example, a cell may be exposed to a chemical species that may bring about a change in one or more characteristics of the cell. In some cases, a stimulus may be used to change one or more characteristics of a cell. For example, upon application of the stimulus, one or more characteristics of a cell may be changed. The stimulus may be, for example, a thermal stimulus, a photo stimulus, a chemical stimulus, or another stimulus. In some cases, conditions sufficient to change the one or more characteristics of a cell may comprise one or more different conditions, such as a temperature and a pressure, a pH and a salt concentration, a chemical species and a temperature, or any other combination of conditions. A temperature sufficient for changing one or more characteristics of the cell may be, for example, at least about 0 degrees Celsius (C), 1° C., 2° C., 3° C., 4° C., 5° C., 10° C., or higher. For example, the temperature may be about 4° C. In other cases, a temperature sufficient for changing one or more characteristics of the cell may be, for example, at least about 25° C., 30° C., 35° C., 37° C., 40° C., 45° C., 50° C., or higher. For example, the temperature may be about 37° C. A pH sufficient for changing one or more characteristics of the cell may be, for example, between about 5 and 8, such as between about 6 and 7.

A biological sample may include a plurality of cells having different dimensions and features. In some cases, processing of the biological sample, such as cell separation and sorting (e.g., as described herein), may affect the distribution of dimensions and cellular features included in the sample by depleting cells having certain features and dimensions and/or isolating cells having certain features and dimensions.

A sample may undergo one or more processes in preparation for analysis (e.g., as described herein), including, but not limited to, filtration, selective precipitation, purification, centrifugation, permeabilization, isolation, agitation, heating, and/or other processes. For example, a sample may be filtered to remove a contaminant or other materials. In an example, a filtration process may comprise the use of microfluidics (e.g., to separate analyte carriers of different sizes, types, charges, or other features).

In an example, a sample comprising one or more cells may be processed to separate the one or more cells from other materials in the sample (e.g., using centrifugation and/or another process). In some cases, cells and/or cellular constituents of a sample may be processed to separate and/or sort groups of cells and/or cellular constituents, such as to separate and/or sort cells and/or cellular constituents of different types. Examples of cell separation include, but are not limited to, separation of white blood cells or immune cells from other blood cells and components, separation of circulating tumor cells from blood, and separation of bacteria from bodily cells and/or environmental materials. A separation process may comprise a positive selection process (e.g., targeting of a cell type of interest for retention for subsequent downstream analysis, such as by use of a monoclonal antibody that targets a surface marker of the cell type of interest), a negative selection process (e.g., removal of one or more cell types and retention of one or more other cell types of interest), and/or a depletion process (e.g., removal of a single cell type from a sample, such as removal of red blood cells from peripheral blood mononuclear cells). Separation of one or more different types of cells may comprise, for example, centrifugation, filtration, microfluidic-based sorting, flow cytometry, fluorescence-activated cell sorting (FACS), magnetic-activated cell sorting (MACS), buoyancy-activated cell sorting (BACS), or any other useful method. For example, a flow cytometry method may be used to detect cells and/or cellular constituents based on a parameter such as a size, morphology, or protein expression. Flow cytometry-based cell sorting may comprise injecting a sample into a sheath fluid that conveys the cells and/or cellular constituents of the sample into a measurement region one at a time. In the measurement region, a light source such as a laser may interrogate the cells and/or cellular constituents and scattered light and/or fluorescence may be detected and converted into digital signals. A nozzle system (e.g., a vibrating nozzle system) may be used to generate droplets (e.g., aqueous droplets) comprising individual cells and/or cellular constituents. Droplets including cells and/or cellular constituents of interest (e.g., as determined via optical detection) may be labeled with an electric charge (e.g., using an electrical charging ring), which charge may be used to separate such droplets from droplets including other cells and/or cellular constituents. For example, FACS may comprise labeling cells and/or cellular constituents with fluorescent markers (e.g., using internal and/or external biomarkers). Cells and/or cellular constituents may then be measured and identified one by one and sorted based on the emitted fluorescence of the marker or absence thereof. MACS may use micro- or nano-scale magnetic particles to bind to cells and/or cellular constituents (e.g., via an antibody interaction with cell surface markers) to facilitate magnetic isolation of cells and/or cellular constituents of interest from other components of a sample (e.g., using a column-based analysis). BACS may use microbubbles (e.g., glass microbubbles) labeled with antibodies to target cells of interest. Cells and/or cellular components coupled to microbubbles may float to a surface of a solution, thereby separating target cells and/or cellular components from other components of a sample. Cell separation techniques may be used to enrich for populations of cells of interest (e.g., prior to partitioning, as described herein). For example, a sample comprising a plurality of cells including a plurality of cells of a given type may be subjected to a positive separation process. The plurality of cells of the given type may be labeled with a fluorescent marker (e.g., based on an expressed cell surface marker or another marker) and subjected to a FACS process to separate these cells from other cells of the plurality of cells. The selected cells may then be subjected to subsequent partition-based analysis (e.g., as described herein) or other downstream analysis. The fluorescent marker may be removed prior to such analysis or may be retained. The fluorescent marker may comprise an identifying feature, such as a nucleic acid barcode sequence and/or unique molecular identifier.

In another example, a first sample comprising a first plurality of cells including a first plurality of cells of a given type (e.g., immune cells expressing a particular marker or combination of markers) and a second sample comprising a second plurality of cells including a second plurality of cells of the given type may be subjected to a positive separation process. The first and second samples may be collected from the same or different subjects, at the same or different types, from the same or different bodily locations or systems, using the same or different collection techniques. For example, the first sample may be from a first subject and the second sample may be from a second subject different than the first subject. The first plurality of cells of the first sample may be provided a first plurality of fluorescent markers configured to label the first plurality of cells of the given type. The second plurality of cells of the second sample may be provided a second plurality of fluorescent markers configured to label the second plurality of cells of the given type. The first plurality of fluorescent markers may include a first identifying feature, such as a first barcode, while the second plurality of fluorescent markers may include a second identifying feature, such as a second barcode, that is different than the first identifying feature. The first plurality of fluorescent markers and the second plurality of fluorescent markers may fluoresce at the same intensities and over the same range of wavelengths upon excitation with a same excitation source (e.g., light source, such as a laser). The first and second samples may then be combined and subjected to a FACS process to separate cells of the given type from other cells based on the first plurality of fluorescent markers labeling the first plurality of cells of the given type and the second plurality of fluorescent markers labeling the second plurality of cells of the given type. Alternatively, the first and second samples may undergo separate FACS processes and the positively selected cells of the given type from the first sample and the positively selected cells of the given type from the second sample may then be combined for subsequent analysis. The encoded identifying features of the different fluorescent markers may be used to identify cells originating from the first sample and cells originating from the second sample. For example, the first and second identifying features may be configured to interact (e.g., in partitions, as described herein) with nucleic acid barcode molecules (e.g., as described herein) to generate barcoded nucleic acid products detectable using, e.g., nucleic acid sequencing.

Fixed Samples

A sample may be a fixed sample. For example, a sample may comprise a plurality of fixed samples, such as a plurality of fixed cells or fixed nuclei. Alternatively or in addition, a sample may comprise a fixed tissue. Fixation of cell or cellular constituent, or a tissue comprising a plurality of cells or nuclei, may comprise application of a chemical species or chemical stimulus. The term "fixed" as used herein with regard to biological samples generally refers to the state of being preserved from decay and/or degradation. "Fixation" generally refers to a process that results in a fixed sample, and in some instances can include contacting the biomolecules within a biological sample with a fixative (or fixation reagent) for some amount of time, whereby the fixative results in covalent bonding interactions such as crosslinks between biomolecules in the sample. A "fixed biological sample" may generally refer to a biological sample that has been contacted with a fixation reagent or fixative. For example, a formaldehyde-fixed biological sample has been contacted with the fixation reagent formaldehyde. "Fixed cells" or "fixed tissues" generally refer to cells or tissues that have been in contact with a fixative under conditions sufficient to allow or result in the formation of intra- and inter-molecular covalent crosslinks between biomolecules in the biological sample. Generally, contact of biological sample (e.g., a cell or nucleus) with a fixation reagent (e.g., paraformaldehyde or PFA) results in the formation of intra- and inter-molecular covalent crosslinks between biomolecules in the biological sample. In some cases, provision of the fixation reagent, such as formaldehyde, may result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

In some embodiments, the fixative or fixation reagent useful for fixing samples is formaldehyde. The term "formaldehyde" when used in the context of a fixative may also refer to "paraformaldehyde" (or "PFA") and "formalin", both of which are terms with specific meanings related to the formaldehyde composition (e.g., formalin is a mixture of formaldehyde and methanol). Thus, a formaldehyde-fixed biological sample may also be referred to as formalin-fixed or PFA-fixed. Protocols and methods for the use of formaldehyde as a fixation reagent to prepare fixed biological samples are well known in the art and can be used in the methods and compositions of the present disclosure. For example, suitable ranges of formaldehyde concentrations for use in preparing a fixed biological sample is 0.1 to 10%, 1-8%, 1-4%, 1-2%, 3-5%, or 3.5-4.5%. In some embodiments of the present disclosure the biological sample is fixed using a final concentration of 1% formaldehyde, 4% formaldehyde, or 10% formaldehyde. Typically, the formaldehyde is diluted from a more concentrated stock solution—e.g., a 35%, 25%, 15%, 10%, 5% PFA stock solution.

Other examples of fixatives include, for example, organic solvents such as alcohols (e.g., methanol or ethanol), ketones (e.g., acetone), and aldehydes (e.g., paraformaldehyde, formaldehyde (e.g., formalin), or glutaraldehyde). As described herein, cross-linking agents may also be used for fixation including, without limitation, disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a cross-linking agent may be a cleavable cross-linking agent (e.g., thermally cleavable, photocleavable, etc.).

In some cases, more than one fixation reagent can be used in combination when preparing a fixed biological sample. For example, a first fixation agent, such as an organic solvent, may be used in combination with a second fixation agent, such as a cross-linking agent. The organic solvent may be an alcohol (e.g., ethanol or methanol), ketone (e.g., acetone), or aldehyde (e.g., paraformaldehyde, formaldehyde, or glutaraldehyde). The cross-linking agent may be selected from the group consisting of disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a first fixation agent may be provided to or brought into contact with the cell to bring about a change in a first characteristic or set of characteristics of the cell, and a fixation agent may be provided to or brought into contact with the cell to bring about a change in a second characteristic or set of characteristics of the cell. For example, a first fixation agent may be provided to or brought into contact with a cell to bring about a change in a dimension of the cell (e.g., a reduction in cross-sectional diameter, see, e.g., U.S. Pat. Pub. No. 2020/0033237, which is incorporated herein by reference in its entirety), and a second fixation agent may be provided to or brought into contact with a cell to bring about a change in a second characteristic or set of characteristics of the cell (e.g., forming crosslinks within and/or surrounding the cell). The first and second fixation agents may be provided to or brought into contact with the cell at the same or different times.

In an example, a first fixation agent that is an organic solvent may be provided to a cell to change a first characteristic (e.g., cell size) and a second fixation agent that is a cross-linking agent may be provided to a cell to change a second characteristic (e.g., cell fluidity or rigidity). The first fixation agent may be provided to the cell before the second fixation agent.

In another embodiment, biomolecules (e.g., biological samples such as tissue specimens) are contacted with a fixation reagent containing both formaldehyde and glutaraldehyde, and thus the contacted biomolecules can include fixation crosslinks resulting both from formaldehyde induced fixation and glutaraldehyde induced fixation. Typically, a suitable concentration of glutaraldehyde for use as a fixation reagent can be 0.1 to 1%.

Changes to a characteristic or a set of characteristics of a cell or cellular constituents (e.g., incurred upon interaction with one or more fixation agents) may be at least partially reversible (e.g., via rehydration or de-crosslinking). Alternatively, changes to a characteristic or set of characteristics of a cell or cellular constituents (e.g., incurred upon interaction with one or more fixation agents) may be substantially irreversible.

A sample (e.g., a cell sample) may be subjected to a fixation process at any useful point in time. For example, cells and/or cellular constituents of a sample may be subjected to a fixation process involving one or more fixation agents (e.g., as described herein) prior to commencement of any subsequent processing, such as for storage. Cells and/or cellular constituents, such as cells and/or cellular constituents of a tissue sample, subjected to a fixation process prior to storage, may be stored in an aqueous solution, optionally in combination with one or more preserving agents configured to preserve morphology, size, or other features of the cells and/or cellular components. Fixed cells and/or cellular constituents may be stored below room temperature, such as in a freezer. Alternatively, cells and/or cellular constituents of a sample may be subjected to a fixation process involving one or more fixation agents subsequent to one or more other processes, such as filtration, centrifugation, agitation, selective precipitation, purification, permeabilization, isolation, heating, etc. For example, cells, nuclei, and/or cellular constituents of a given type from a sample may be subjected to a fixation process following a separation and/or enrichment procedure (e.g., as described herein). In an example, a sample comprising a plurality of cells including a plurality of cells of a given type may be subjected to a positive separation process to provide a sample enriched in the plurality of cells of the given type. The enriched sample may then be subjected to a fixation process involving one or more fixation agents (e.g., as described herein) to provide an enriched sample comprising a plurality of fixed cells. A fixation process may be performed in a bulk solution. In some cases, fixed samples (e.g., fixed cells, fixed nuclei, and/or cellular constituents) may be partitioned amongst a plurality of partitions (e.g., droplets or wells) and subjected to processing as described elsewhere herein. In some cases, fixed samples may undergo additional processing, such as partial or complete reversal of a fixation process by, for example, rehydration or de-crosslinking, prior to partitioning and any subsequent processing. In some cases, fixed samples may undergo partial or complete reversal of a fixation process within a plurality of partitions (e.g., prior to or concurrent with additional processing described elsewhere herein).

In some cases, a tissue specimen comprising a plurality of cells and/or cellular constituents may be processed to provide formalin-fixed paraffin-embedded (FFPE) tissue. A tissue specimen may be contacted (e.g., saturated) with formalin and then embedded in paraffin wax. FFPE processing may facilitate preservation of a tissue sample (e.g., prior to subsequent processing and analysis). A tissue sample, including an FFPE tissue sample, may additionally or alternatively be subjected to storage in a low-temperature freezer. Cells and/or cellular constituents may be dissociated from a tissue sample (e.g., FFPE tissue sample) prior to undergoing subsequent processing. In some cases, individual cells and/or cellular constituents of a tissue sample such as an FFPE tissue sample may be optically detected, labeled, or otherwise processed prior to any such dissociation. Such detection, labeling, or other processing may be performed according to a 2- or 3-dimensional array and optionally according to a pre-determined pattern.

Targeting and RNA templated ligation

The methods described herein may comprise templated ligation or RNA targeting. A templated ligation process may comprise contacting a nucleic acid molecule (e.g., an RNA molecule) with a probe molecule. The probe molecule may interact with one or more other probe molecules, for example, comprising a barcode sequence, to generate a probe-barcode complex. An extension reaction may be performed on at least a portion of the probe-barcode complex to generate a nucleic acid product that comprises the barcode sequence and is associated with a sequence of the nucleic acid molecule. Beneficially, the methods described herein may allow barcoding of the nucleic acid molecule without performing reverse transcription on the nucleic acid molecule. The methods herein may comprise ligation-mediated reactions.

A method may comprise contacting a nucleic acid molecule (e.g., an RNA molecule) with a first probe molecule, comprising a first sequence and a second sequence, under conditions sufficient for the first sequence to hybridize to a sequence of the nucleic acid molecule. A second probe molecule comprising a third sequence may hybridize to the second sequence of the first probe molecule. The first probe or the second probe molecule may comprise a barcode sequence (e.g., as described herein). For example, the second probe molecule may be a nucleic acid molecule (e.g., as described herein). In some cases, a splint molecule may be used to link the first and second probe molecules. For example, a fourth sequence of the splint molecule may hybridize to the second sequence of the first probe molecule and a fifth sequence of the splint molecule may hybridize to the third sequence of the second probe molecule.

In another example, a first probe molecule with a first reactive moiety and a second probe molecule with a second reactive moiety may be used. A first sequence of the first probe molecule may hybridize to a first sequence of a nucleic acid molecule and a second sequence of the second probe molecule may hybridize to a second sequence of the nucleic acid molecule. The first and second sequences of the nucleic acid molecule may be adjacent or may be separated by a gap of one or more nucleotides, which gap may optionally be filled (e.g., using a polymerase). The first reactive moiety of the first probe molecule and the second reactive moiety of the second probe molecule may be subjected to conditions sufficient for the first and second reactive moieties to react to provide a linking moiety. For example, a click chemistry reaction involving an alkyne moiety and an azide moiety may be used to provide a triazole linking moiety. In other examples, an iodide moiety may be chemically ligated to a phosphorothioate moiety to form a phosphorothioate bond, an acid may be ligated to an amine to form an amide bond, or a phosphate may be ligated to an amine to form a phosphoramidate bond. In some cases, the probes may be subjected to an enzymatic ligation reaction, using a ligase, e.g., SplintR ligases, T4 ligases, KOD ligases, PBCVI enzymes, etc. to form a probe-linked nucleic acid molecule. Where the two probes are non-adjacent, gap regions between the probes may be filled prior to ligation. In some instances, ribonucleotides or deoxyribonucleotides are ligated between the first and second probes.

Prior to, in parallel, or subsequent to linking of the first and second probe molecules (e.g., via reaction between their respective reactive moieties), a third probe molecule (e.g., a nucleic acid barcode molecule) may be subjected to conditions sufficient to hybridize to a third sequence of the first probe molecule. The third probe molecule may comprise a barcode sequence. In some cases, a splint molecule may be used to link the first and third probe molecules. In some cases, the first and second probe molecules may be linked to one another such that a loop or "padlock" is formed after hybridization of the first sequence of the first probe molecule to the first sequence of the nucleic acid molecule and the second sequence of the second probe molecule to the second sequence of the nucleic acid molecule. A linkage between the first and second probe molecules may be generated after hybridization of the first and second probe molecules to the nucleic acid molecule, such as via reaction between two reactive moieties to form a linking moiety. Alternatively, the first and second probe molecules may be linked to one another before the first and second probe molecules hybridize to the nucleic acid molecule.

All or a portion of the templated ligation processes described herein may be performed within a partition (e.g., as described herein). Alternatively, one or more such processes may be performed within a bulk solution. For example, one or more probe molecules may be subjected to conditions sufficient to hybridize to a nucleic acid molecule (e.g., a nucleic acid molecule included in an analyte carrier such as a cell) within a bulk solution. The nucleic acid molecule may be partitioned within various reagents (e.g., as described herein) including a nucleic acid barcode molecule, such as a nucleic acid barcode molecule releasably coupled to a bead (e.g., as described herein). Within the partition, the nucleic acid barcode molecule may hybridize to a sequence of a probe molecule hybridized to the nucleic acid molecule, thereby generated a barcode-linked nucleic acid molecule. Templated ligation processes may permit indirect barcoding of a nucleic acid molecule without the use of reverse transcription. Details of such processes and additional schemes are included in, for example, International Patent Publication No. WO2019/165318, which is herein entirely incorporated by reference for all purposes.

The methods provided herein may comprise the use of an RNA targeting process to, e.g., enrich selected nucleic acid molecules within a sample. A method may comprise providing a plurality of barcoded nucleic acid molecules (e.g., barcoded RNA molecules) comprising a plurality of different barcode sequences, identifying a barcode sequence of the plurality of different barcode sequences, and enriching barcoded nucleic acid molecules comprising the barcode sequence. Enriching may comprise performing a nucleic acid extension reaction using a barcoded nucleic acid molecule comprising the barcode sequence and a primer comprising a sequence specific for the barcode sequence to generate an enriched plurality of barcoded nucleic acid molecules comprising the barcode sequence of interest. An additional nucleic acid extension reaction may be performed using primers comprising sequences specific for, e.g., sequencing handles attached to the barcoded nucleic acid molecule. A primer used in an enrichment reaction may comprise an affinity group, which affinity group may be used to separate a barcoded nucleic acid molecule comprising the barcode sequence of interest from other barcoded nucleic acid molecules of the plurality of barcoded nucleic acid molecules via interaction between the affinity group and a capture moiety. For example, a magnetic interaction may be used to separate a barcoded nucleic acid molecule comprising the barcode sequence of interest from other barcoded nucleic acid molecules of the plurality of barcoded nucleic acid molecules. Enrichment of barcoded nucleic acid molecules may be performed in a bulk solution subsequent to in-partition processing of a plurality of nucleic acid molecules (e.g., as described herein). Such targeting processes may permit enrichment of nucleic acid molecules of interest within a population of nucleic acid molecules, such as a population of nucleic acid molecules barcoded according to the methods provided herein. Details of such processes and additional schemes are included in, for example, International Patent Application No. PCT/US2020/012413, which is herein entirely incorporated by reference for all purposes.

Multiplexing & 5'

The present disclosures provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize analyte carriers and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S.

Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In some aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more analyte carriers may be used to characterize an analyte carrier as belonging to a particular set of analyte carriers. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling an analyte carrier may comprise subjecting the antibody-linked barcode molecule or the epitope binding fragment-linked barcode molecule to conditions suitable for binding the antibody to a molecule present on a surface of the analyte carrier. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 µM, 90 µM. 80 µM, 70 µM, 60 µM, 50 µM, 40 µM, 30 µM, 20 µM, 10 µM, 9 µM, 8 AM, 7 µM, 6 µM, 5 M, 4 PM, 3 µM, 2 µM, 1 µM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 µM, 800 µM, 700 µM, 600 µM, 500 µM, 400 µM, 300 µM, 200 µM, 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, or 1 µM. For example, the dissociation constant may be less than about 10 µM.

In another example, a reporter oligonucleotide may be coupled to a cell-penetrating peptide (CPP), and labeling cells may comprise delivering the CPP coupled reporter oligonucleotide into an analyte carrier. Labeling analyte carriers may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells may comprise subjecting the fluorophore-linked barcode molecule to conditions suitable for binding the fluorophore to the surface of the analyte carrier. In some instances, fluorophores can interact strongly with lipid bilayers and labeling analyte carriers may comprise subjecting the fluorophore-linked barcode molecule to conditions such that the fluorophore binds to or is inserted into a membrane of the analyte carrier. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B. Alexa 594 maleimide, Texas Red maleimide, Alexa 633 maleimide, Abberior STAR 63SP azide, Atto 647N maleimide, Atto 647 SE, or Sulfo-Cy5 maleimide. See, e.g., Hughes L D, et al. PLOS One. 2014 Feb. 4: 9(2): e87649, which is hereby incorporated by reference in its entirety for all purposes, for a description of organic fluorophores.

A reporter oligonucleotide may be coupled to a lipophilic molecule, and labeling analyte carriers may comprise delivering the nucleic acid barcode molecule to a membrane of the analyte carrier or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and analyte carrier may be such that the analyte carrier retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular analyte carrier, population, or sample. The analyte carriers may be incubated with a plurality of libraries and a given analyte carrier may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 11:
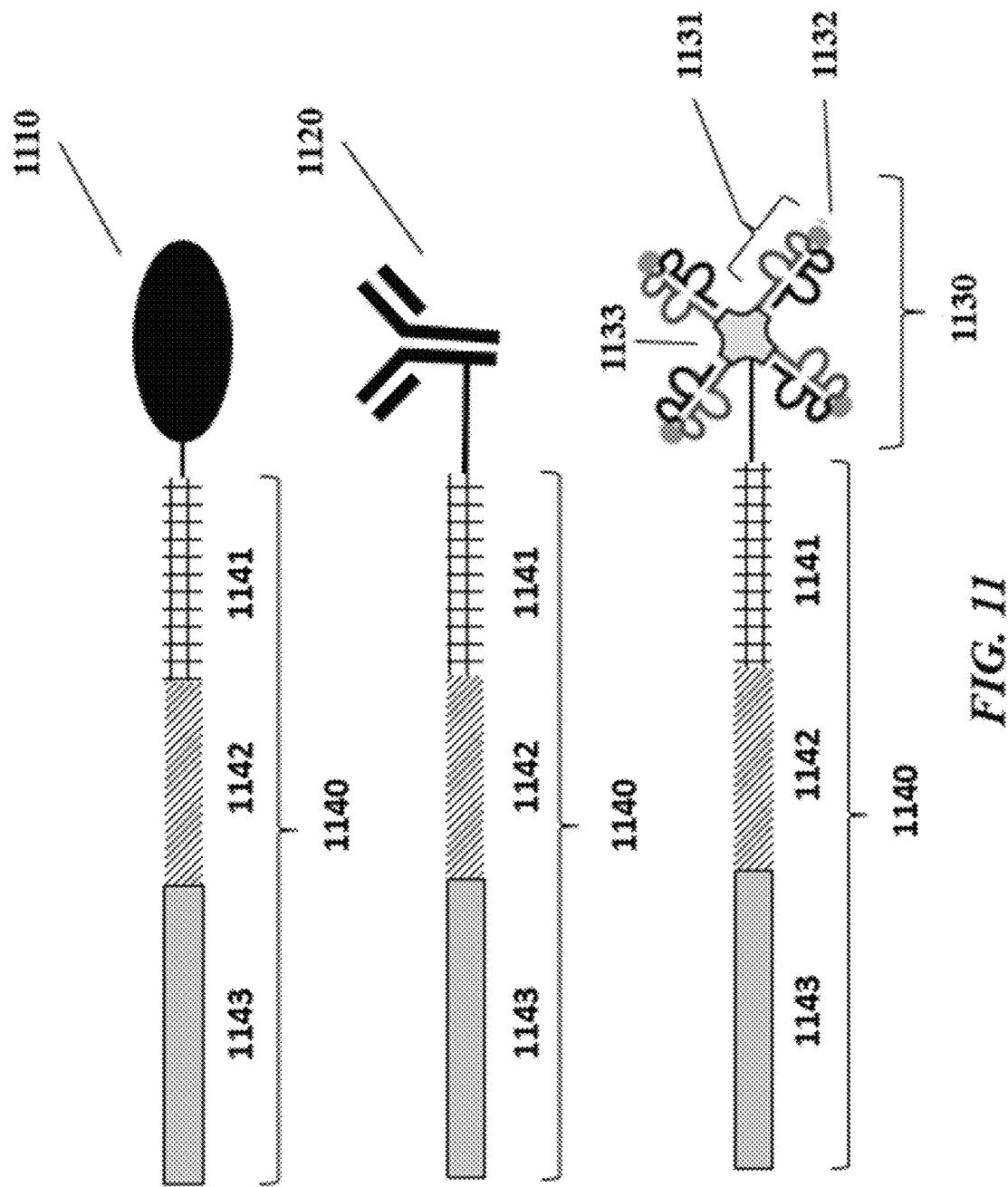
FIG. 11 schematically illustrates example labelling agents with nucleic acid molecules attached thereto.

FIG. 11 describes exemplary labelling agents (1110, 1120, 1130) comprising reporter oligonucleotides (1140) attached thereto. Labelling agent 1110 (e.g., any of the labelling agents described herein) is attached (either directly, e.g., covalently attached, or indirectly) to reporter oligonucleotide 1140. Reporter oligonucleotide 1140 may comprise barcode sequence 1142 that identifies labelling agent 1110. Reporter oligonucleotide 1140 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 11, in some instances, reporter oligonucleotide 1140 conjugated to a labelling agent (e.g., 1110, 1120, 1130) comprises a primer sequence 1141, a barcode sequence that identifies the labelling agent (e.g., 1110, 1120, 1130), and functional sequence 1143. Functional sequence 1143 may be configured to hybridize to a complementary sequence, such as a complementary sequence present on a nucleic acid barcode molecule 1190 (not shown), such as those described elsewhere herein. In some instances, nucleic acid barcode molecule 1190 is attached to a support (e.g., a bead, such as a gel bead), such as those described elsewhere herein. For example, nucleic acid barcode molecule 1190 may be attached to the support via a releasable linkage (e.g., comprising a labile bond), such as those described elsewhere herein. In some instances, reporter oligonucleotide 1140 comprises one or more additional functional sequences, such as those described above.

In some instances, the labelling agent 1110 is a protein or polypeptide (e.g., an antigen or prospective antigen) comprising reporter oligonucleotide 1140. Reporter oligonucleotide 1140 comprises barcode sequence 1142 that identifies polypeptide 1110 and can be used to infer the presence of an analyte, e.g., a binding partner of polypeptide 1110 (i.e., a molecule or compound to which polypeptide 1110 can bind). In some instances, the labelling agent 1110 is a lipophilic moiety (e.g., cholesterol) comprising reporter oligonucleotide 1140, where the lipophilic moiety is selected such that labelling agent 1110 integrates into a membrane of a cell or nucleus. Reporter oligonucleotide 1140 comprises barcode sequence 1142 that identifies lipophilic moiety 1110 which in some instances is used to tag cells (e.g., groups of cells, cell samples, etc.) and may be used for multiplex analyses as described elsewhere herein. In some instances, the labelling agent is an antibody 1120 (or an epitope binding fragment thereof) comprising reporter oligonucleotide 1140. Reporter oligonucleotide 1140 comprises barcode sequence 1142 that identifies antibody 1120 and can be used to infer the presence of, e.g., a target of antibody 1120 (i.e., a molecule or compound to which antibody 1120 binds). In other embodiments, labelling agent 1130 comprises an MHC molecule 1131 comprising peptide 1132 and reporter oligonucleotide 1140 that identifies peptide 1132. In some instances, the MHC molecule is coupled to a support 1133. In some instances, support 1133 may be a polypeptide, such as streptavidin, or a polysaccharide, such as dextran. In some instances, reporter oligonucleotide 1140 may be directly or indirectly coupled to MHC labelling agent 1130 in any suitable manner. For example, reporter oligonucleotide 1140 may be coupled to MHC molecule 1131, support 1133, or peptide 1132. In some embodiments, labelling agent 1130 comprises a plurality of MHC molecules, (e.g. is an MHC multimer, which may be coupled to a support (e.g., 1133)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 12A:
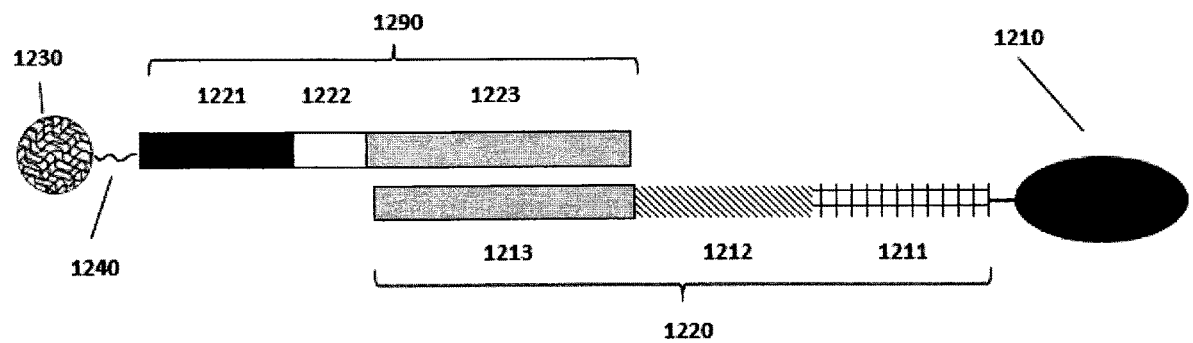
FIG. 12A schematically shows an example of labelling agents.
Figure 12B:
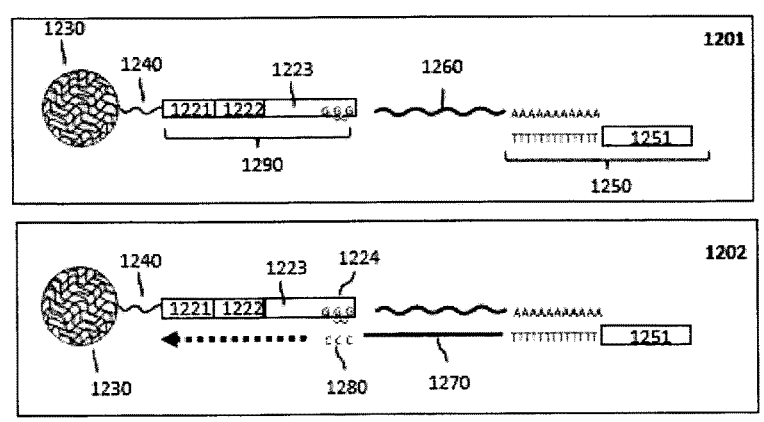
FIG. 12B schematically shows another example workflow for processing nucleic acid molecules.
Figure 12C:
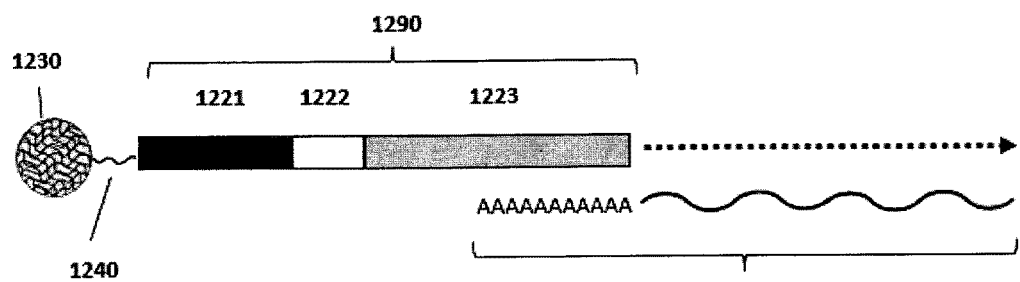
FIG. 12C schematically shows another example workflow for processing nucleic acid molecules.
Figure 13:
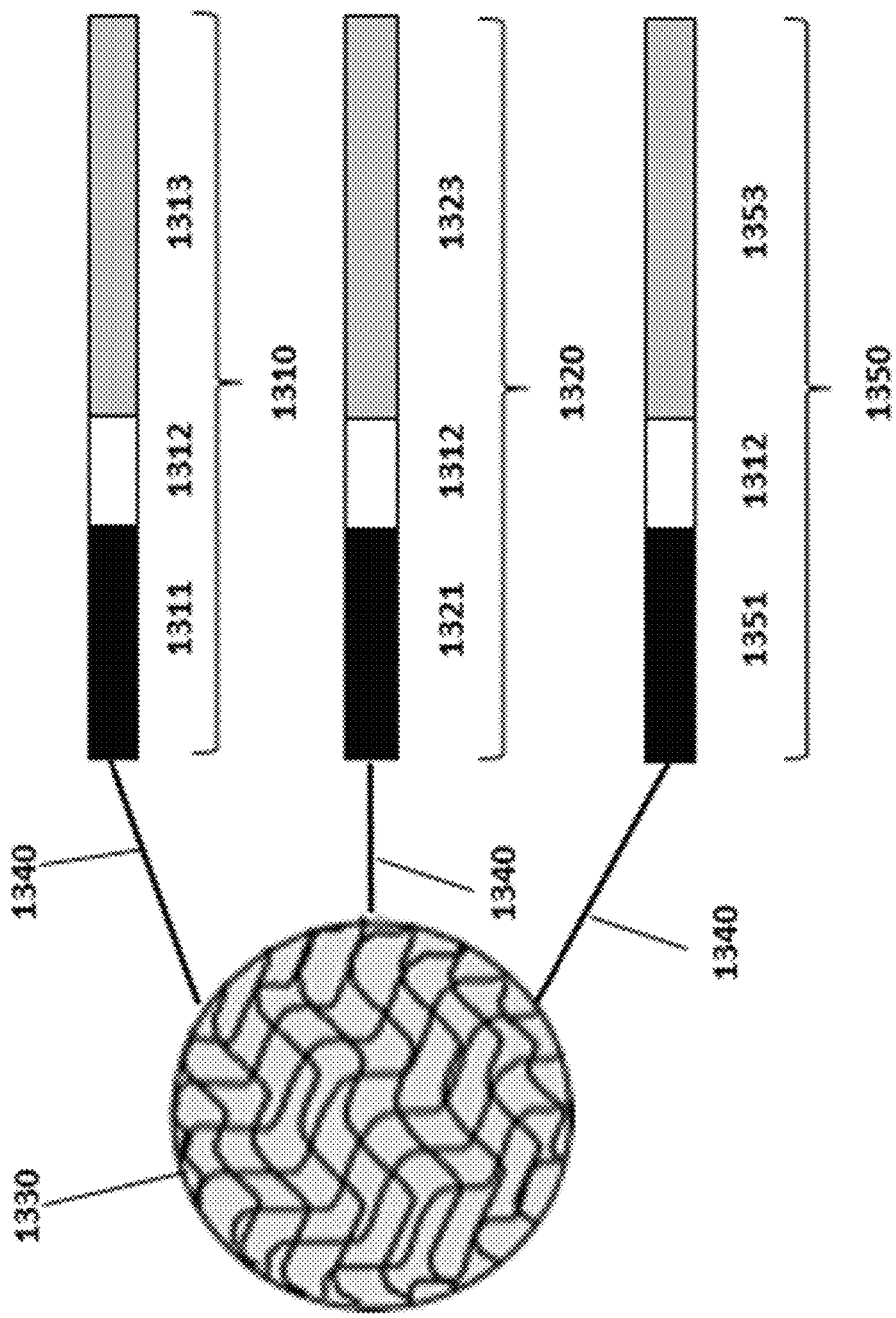
FIG. 13 schematically shows another example of a barcode-carrying bead.

FIG. 13 illustrates another example of a barcode carrying bead. In some embodiments, analysis of multiple analytes (e.g., RNA and one or more analytes using labelling agents described herein) may comprise nucleic acid barcode molecules as generally depicted in FIG. 13. In some embodiments, nucleic acid barcode molecules 1310 and 1320 are attached to support 1330 via a releasable linkage 1340 (e.g., comprising a labile bond) as described elsewhere herein. Nucleic acid barcode molecule 1310 may comprise adapter sequence 1311, barcode sequence 1312 and adapter sequence 1313. Nucleic acid barcode molecule 1320 may comprise adapter sequence 1321, barcode sequence 1312, and adapter sequence 1323, wherein adapter sequence 1323 comprises a different sequence than adapter sequence 1313. In some instances, adapter 1311 and adapter 1321 comprise the same sequence. In some instances, adapter 1311 and adapter 1321 comprise different sequences. Although support 1330 is shown comprising nucleic acid barcode molecules 1310 and 1320, any suitable number of barcode molecules comprising common barcode sequence 1312 are contemplated herein. For example, in some embodiments, support 1330 further comprises nucleic acid barcode molecule 1350. Nucleic acid barcode molecule 1350 may comprise adapter sequence 1351, barcode sequence 1312 and adapter sequence 1353, wherein adapter sequence 1353 comprises a different sequence than adapter sequence 1313 and 1323. In some instances, nucleic acid barcode molecules (e.g., 1310, 1320, 1350) comprise one or more additional functional sequences, such as a UMI or other sequences described herein. The nucleic acid barcode molecules 1310, 1320 or 1350 may interact with analytes as described elsewhere herein, for example, as depicted in FIGS. 12A-C.

Referring to FIG. 12A, in an instance where cells are labelled with labeling agents, sequence 1223 may be complementary to an adapter sequence of a reporter oligonucleotide. Cells may be contacted with one or more reporter oligonucleotide 1220 conjugated labelling agents 1210 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 1210 which is conjugated to oligonucleotide 1220 and support 1230 (e.g., a bead, such as a gel bead) comprising nucleic acid barcode molecule 1290 is partitioned into a partition amongst a plurality of partitions (e.g., a droplet of a droplet emulsion or a well of a microwell array). In some instances, the partition comprises at most a single cell bound to labelling agent 1210. In some instances, reporter oligonucleotide 1220 conjugated to labelling agent 1210 (e.g., polypeptide, an antibody, pMHC molecule such as an MHC multimer, etc.) comprises a first adapter sequence 1211 (e.g., a primer sequence), a barcode sequence 1212 that identifies the labelling agent 1210 (e.g., the polypeptide, antibody, or peptide of a pMHC molecule or complex), and an adapter sequence 1213. Adapter sequence 1213 may be configured to hybridize to a complementary sequence, such as sequence 1223 present on a nucleic acid barcode molecule 1290. In some instances, oligonucleotide 1220 comprises one or more additional functional sequences, such as those described elsewhere herein.

Barcoded nucleic may be generated (e.g., via a nucleic acid reaction, such as nucleic acid extension or ligation) from the constructs described in FIGS. 12A-C. For example, sequence 1213 may then be hybridized to complementary sequence 1223 to generate (e.g., via a nucleic acid reaction, such as nucleic acid extension or ligation) a barcoded nucleic acid molecule comprising cell (e.g., partition specific) barcode sequence 1222 (or a reverse complement thereof) and reporter barcode sequence 1212 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 12A-C, or a combination of workflows for an individual analyte, as described elsewhere herein. For example, by using a combination of the workflows as generally depicted in FIGS. 12A-C, multiple analytes can be analyzed.

In some instances, analysis of an analyte (e.g. a nucleic acid, a polypeptides, a carbohydrate, a lipid, etc.) comprises a workflow as generally depicted in FIG. 12A. A nucleic acid barcode molecule 1290 may be co-partitioned with the one or more analytes. In some instances, nucleic acid barcode molecule 1290 is attached to a support 1230 (e.g., a bead, such as a gel bead), such as those described elsewhere herein. For example, nucleic acid barcode molecule 1290 may be attached to support 1230 via a releasable linkage 1240 (e.g., comprising a labile bond), such as those described elsewhere herein. Nucleic acid barcode molecule 1290 may comprise a barcode sequence 1221 and optionally comprise other additional sequences, for example, a UMI sequence 1222 (or other functional sequences described elsewhere herein). The nucleic acid barcode molecule 1290 may comprise a sequence 1223 that may be complementary to another nucleic acid sequence, such that it may hybridize to a particular sequence.

For example, sequence 1223 may comprise a poly-T sequence and may be used to hybridize to mRNA. Referring to FIG. 12C, in some embodiments, nucleic acid barcode molecule 1290 comprises sequence 1223 complementary to a sequence of RNA molecule 1260 from a cell. In some instances, sequence 1223 comprises a sequence specific for an RNA molecule. Sequence 1223 may comprise a known or targeted sequence or a random sequence. In some instances, a nucleic acid extension reaction may be performed, thereby generating a barcoded nucleic acid product comprising sequence 1223, the barcode sequence 1221, UMI sequence 1222, any other functional sequence, and a sequence corresponding to the RNA molecule 1260.

In another example, sequence 1223 may be complementary to an overhang sequence or an adapter sequence that has been appended to an analyte. For example, referring to FIG. 12B, panel 1201, in some embodiments, primer 1250 comprises a sequence complementary to a sequence of nucleic acid molecule 1260 (such as an RNA encoding for a BCR sequence) from an analyte carrier. In some instances, primer 1250 comprises one or more sequences 1251 that are not complementary to RNA molecule 1260. Sequence 1251 may be a functional sequence as described elsewhere herein, for example, an adapter sequence, a sequencing primer sequence, or a sequence the facilitates coupling to a flow cell of a sequencer. In some instances, primer 1250 comprises a poly-T sequence. In some instances, primer 1250 comprises a sequence complementary to a target sequence in an RNA molecule. In some instances, primer 1250 comprises a sequence complementary to a region of an immune molecule, such as the constant region of a TCR or BCR sequence. Primer 1250 is hybridized to nucleic acid molecule 1260 and complementary molecule 1270 is generated (see Panel 1202). For example, complementary molecule 1270 may be cDNA generated in a reverse transcription reaction. In some instances, an additional sequence may be appended to complementary molecule 1270. For example, the reverse transcriptase enzyme may be selected such that several non-templated bases 1280 (e.g., a poly-C sequence) are appended to the cDNA. In another example, a terminal transferase may also be used to append the additional sequence. Nucleic acid barcode molecule 1290 comprises a sequence 1224 complementary to the non-templated bases, and the reverse transcriptase performs a template switching reaction onto nucleic acid barcode molecule 1290 to generate a barcoded nucleic acid molecule comprising cell (e.g., partition specific) barcode sequence 1222 (or a reverse complement thereof) and a sequence of complementary molecule 1270 (or a portion thereof). In some instances, sequence 1223 comprises a sequence complementary to a region of an immune molecule, such as the constant region of a TCR or BCR sequence. Sequence 1223 is hybridized to nucleic acid molecule 1260 and a complementary molecule 1270 is generated. For example complementary molecule 1270 may be generated in a reverse transcription reaction generating a barcoded nucleic acid molecule comprising cell (e.g., partition specific) barcode sequence 1222 (or a reverse complement thereof) and a sequence of complementary molecule 1270 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No. 2019/0367969, each of which applications is herein entirely incorporated by reference for all purposes.

Combinatorial Barcoding

In some instances, barcoding of a nucleic acid molecule may be done using a combinatorial approach. In such instances, one or more nucleic acid molecules (which may be comprised in a cell or cell bead) may be partitioned (e.g., in a first set of partitions, e.g., wells or droplets) with one or more first nucleic acid barcode molecules (optionally coupled to a bead). The first nucleic acid barcode molecules or derivative thereof (e.g., complement, reverse complement) may then be attached to the one or more nucleic acid molecules, thereby generating first barcoded nucleic acid molecules, e.g., using the processes described herein. The first nucleic acid barcode molecules may be partitioned to the first set of partitions such that a nucleic acid barcode molecule, of the first nucleic acid barcode molecules, that is in a partition comprises a barcode sequence that is unique to the partition among the first set of partitions. Each partition may comprise a unique barcode sequence. For example, a set of first nucleic acid barcode molecules partitioned to a first partition in the first set of partitions may each comprise a common barcode sequence that is unique to the first partition among the first set of partitions, and a second set of first nucleic acid barcode molecules partitioned to a second partition in the first set of partitions may each comprise another common barcode sequence that is unique to the second partition among the first set of partitions. Such barcode sequence (unique to the partition) may be useful in determining the cell or partition from which the one or more nucleic acid molecules (or derivatives thereof) originated.

The first barcoded nucleic acid molecules from multiple partitions of the first set of partitions may be pooled and re-partitioned (e.g., in a second set of partitions, e.g., one or more wells or droplets) with one or more second nucleic acid barcode molecules. The second nucleic acid barcode molecules or derivative thereof may then be attached to the first barcoded nucleic acid molecules, thereby generating second barcoded nucleic acid molecules. As with the first nucleic acid barcode molecules during the first round of partitioning, the second nucleic acid barcode molecules may be partitioned to the second set of partitions such that a nucleic acid barcode molecule, of the second nucleic acid barcode molecules, that is in a partition comprises a barcode sequence that is unique to the partition among the second set of partitions. Such barcode sequence may also be useful in determining the cell or partition from which the one or more nucleic acid molecules or first barcoded nucleic acid molecules originated. The second barcoded nucleic acid molecules may thus comprise two barcode sequences (e.g., from the first nucleic acid barcode molecules and the second nucleic acid barcode molecules).

Additional barcode sequences may be attached to the second barcoded nucleic acid molecules by repeating the processes any number of times (e.g., in a split-and-pool approach), thereby combinatorially synthesizing unique barcode sequences to barcode the one or more nucleic acid molecules. For example, combinatorial barcoding may comprise at least 1, 2, 3, 4, 5, 6, 7, 8, 9, 10 or more operations of splitting (e.g., partitioning) and/or pooling (e.g., from the partitions). Additional examples of combinatorial barcoding may also be found in International Patent Publication Nos. WO2019/165318, each of which is herein entirely incorporated by reference for all purposes.

Beneficially, the combinatorial barcode approach may be useful for generating greater barcode diversity, and synthesizing unique barcode sequences on nucleic acid molecules derived from a cell or partition. For example, combinatorial barcoding comprising three operations, each with 100 partitions, may yield up to 106 unique barcode combinations. In some instances, the combinatorial barcode approach may be helpful in determining whether a partition contained only one cell or more than one cell. For instance, the sequences of the first nucleic acid barcode molecule and the second nucleic acid barcode molecule may be used to determine whether a partition comprised more than one cell. For instance, if two nucleic acid molecules comprise different first barcode sequences but the same second barcode sequences, it may be inferred that the second set of partitions comprised two or more cells.

In some instances, combinatorial barcoding may be achieved in the same compartment. For instance, a unique nucleic acid molecule comprising one or more nucleic acid bases may be attached to a nucleic acid molecule (e.g., a sample or target nucleic acid molecule) in successive operations within a partition (e.g., droplet or well) to generate a first barcoded nucleic acid molecule. A second unique nucleic acid molecule comprising one or more nucleic acid bases may be attached to the first barcoded nucleic acid molecule molecule, thereby generating a second barcoded nucleic acid molecule. In some instances, all the reagents for barcoding and generating combinatorially barcoded molecules may be provided in a single reaction mixture, or the reagents may be provided sequentially.

In some instances, cell beads comprising nucleic acid molecules may be barcoded. In such cases, the cell beads may be partitioned into a plurality of partitions and subjected to conditions sufficient to attach one or more nucleic acid barcode molecules to the nucleic acid molecules, thereby generating barcoded nucleic acid molecules. As described herein, a partition may comprise a unique nucleic acid barcode sequence that is different from nucleic acid barcode sequences of other partitions; accordingly, the nucleic acid barcode molecule may be used to identify or determine the partition or cell bead from which a nucleic acid molecule originated.

Following attachment of the one or more nucleic acid barcode molecules to the nucleic acid molecules, the cell beads may be removed from the partitions and re-partitioned into an additional plurality of partitions, which may be the same plurality of partitions or a different plurality of partitions. The cell beads may be subjected to conditions sufficient to attach one or more additional nucleic acid barcode molecules to the barcoded nucleic acid molecules, thereby combinatorially synthesizing unique barcode sequences onto the nucleic acid molecules.

In some cases, the cell beads may be removed from the additional plurality of partitions and, in some instances, pooled. Additional partitioning, attachment, removal, and pooling operations may be performed. Combinatorial barcoding may comprise at least 1, 2, 3, 4, 5, 6, 7, 8, 9, 10 or more operations. Such combinatorial barcoding operations may be useful in generating greater barcode diversity and/or for determining the number or origin of cell beads of a particular partition or set of partitions.

Additional examples of combinatorial barcoding are provided in, e.g., U.S. Pat. Pub. No. 2019/0330694, which is herein entirely incorporated by reference for all purposes.
Reagents In accordance with certain aspects, biological particles and/or analyte carriers may be partitioned along with lysis reagents in order to release the contents of the analyte carriers within the partition. In such cases, the lysis agents can be contacted with the analyte carrier suspension concurrently with, or immediately prior to, the introduction of the analyte carriers into the partitioning junction/droplet generation zone (e.g., junction 210), such as through an additional channel or channels upstream of the channel junction. In accordance with other aspects, additionally or alternatively, analyte carriers may be partitioned along with other reagents, as will be described further below.

The methods and systems of the present disclosure may comprise microfluidic devices and methods of use thereof, which may be used for co-partitioning analyte carriers or biological particles with reagents. Such systems and methods are described in U.S. Patent Publication No. US/20190367997, which is herein incorporated by reference in its entirety for all purposes.

Beneficially, when lysis reagents and analyte carriers are co-partitioned, the lysis reagents can facilitate the release of the contents of the analyte carriers within the partition. The contents released in a partition may remain discrete from the contents of other partitions.

As will be appreciated, the channel segments of the microfluidic devices described elsewhere herein may be coupled to any of a variety of different fluid sources or receiving components, including reservoirs, tubing, manifolds, or fluidic components of other systems. As will be appreciated, the microfluidic channel structures may have various geometries and/or configurations. For example, a microfluidic channel structure can have more than two channel junctions. For example, a microfluidic channel structure can have 2, 3, 4, 5 channel segments or more each carrying the same or different types of beads, reagents, and/or analyte carriers that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the analyte carriers to cause the release of the analyte carrier's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion-based partitioning such as encapsulation of analyte carriers that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles or analyte carriers described above, other reagents can also be co-partitioned with the analyte carriers, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles or analyte carriers (e.g., a cell or a nucleus in a polymer matrix), the biological particles or analyte carriers may be exposed to an appropriate stimulus to release the biological particle or analyte carriers or their contents from a co-partitioned bead or microcapsule. For example, in some cases, a chemical stimulus may be co-partitioned along with an encapsulated analyte carrier to allow for the degradation of the bead or microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative examples, this may be a different and non-overlapping stimulus, in order to allow an encapsulated analyte carrier to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the analyte carrier, such as endonucleases to fragment an analyte carrier's DNA, DNA polymerase enzymes and dNTPs used to amplify the analyte carrier's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of analyte carriers, such as RNA, DNA, or proteins) contained therein may be further processed within the partitions. In accordance with the methods and systems described herein, the macromolecular component contents of individual analyte carriers can be provided with unique identifiers such that, upon characterization of those macromolecular components they may be attributed as having been derived from the same analyte carrier or particles. The ability to attribute characteristics to individual analyte carriers or groups of analyte carriers is provided by the assignment of unique identifiers specifically to an individual analyte carrier or groups of analyte carriers. Unique identifiers, e.g., in the form of nucleic acid barcodes can be assigned or associated with individual analyte carriers or populations of analyte carriers, in order to tag or label the analyte carrier's macromolecular components (and as a result, its characteristics) with the unique identifiers. These unique identifiers can then be used to attribute the analyte carrier's components and characteristics to an individual analyte carrier or group of analyte carriers.

In some aspects, this is performed by co-partitioning the individual analyte carrier or groups of analyte carriers with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual analyte carrier, or to other components of the analyte carrier, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned analyte carriers. These sequences include, e.g., targeted or random/universal amplification primer sequences for amplifying nucleic acids (e.g., mRNA, the genomic DNA) from the individual analyte carriers within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of analyte carriers, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 2:
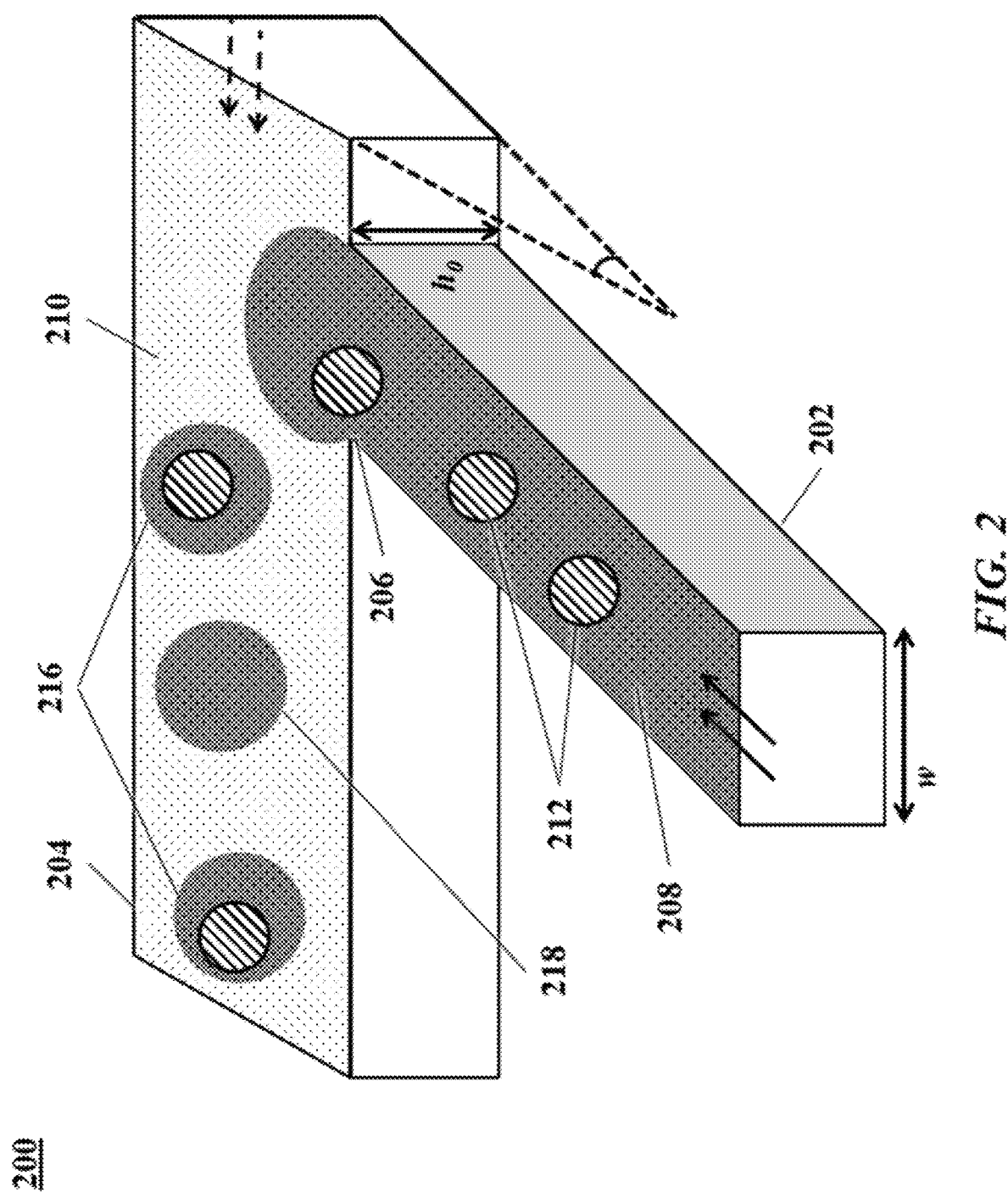
FIG. 2 shows an example of a microfluidic channel structure for the controlled partitioning of beads into discrete droplets.

FIG. 2 shows an example of a microfluidic channel structure for the controlled partitioning of beads into discrete droplets. A channel structure 200 can include a channel segment 202 communicating at a channel junction 206 (or intersection) with a reservoir 204. The reservoir 204 can be a chamber. Any reference to "reservoir," as used herein, can also refer to a "chamber." In operation, an aqueous fluid 208 that includes suspended beads 212 may be transported along the channel segment 202 into the junction 206 to meet a second fluid 210 that is immiscible with the aqueous fluid 208 in the reservoir 204 to create droplets 216, 218 of the aqueous fluid 208 flowing into the reservoir 204. At the junction 206 where the aqueous fluid 208 and the second fluid 210 meet, droplets can form based on factors such as the hydrodynamic forces at the junction 206, flow rates of the two fluids 208, 210, fluid properties, and certain geometric parameters (e.g., w, $h_0$, a, etc.) of the channel structure 200. A plurality of droplets can be collected in the reservoir 204 by continuously injecting the aqueous fluid 208 from the channel segment 202 through the junction 206.

A discrete droplet generated may include a bead (e.g., as in occupied droplets 216). Alternatively, a discrete droplet generated may include more than one bead. Alternatively, a discrete droplet generated may not include any beads (e.g., as in unoccupied droplet 218). In some instances, a discrete droplet generated may contain one or more analyte carriers, as described elsewhere herein. In some instances, a discrete droplet generated may comprise one or more reagents, as described elsewhere herein.

In some instances, the aqueous fluid 208 can have a substantially uniform concentration or frequency of beads 212. The beads 212 can be introduced into the channel segment 202 from a separate channel (not shown in FIG. 2). The frequency of beads 212 in the channel segment 202 may be controlled by controlling the frequency in which the beads 212 are introduced into the channel segment 202 and/or the relative flow rates of the fluids in the channel segment 202 and the separate channel. In some instances, the beads can be introduced into the channel segment 202 from a plurality of different channels, and the frequency controlled accordingly.

In some instances, the aqueous fluid 208 in the channel segment 202 can comprise analyte carriers. In some instances, the aqueous fluid 208 can have a substantially uniform concentration or frequency of analyte carriers. As with the beads, the analyte carriers can be introduced into the channel segment 202 from a separate channel. The frequency or concentration of the analyte carriers in the aqueous fluid 208 in the channel segment 202 may be controlled by controlling the frequency in which the analyte carriers are introduced into the channel segment 202 and/or the relative flow rates of the fluids in the channel segment 202 and the separate channel. In some instances, the analyte carriers can be introduced into the channel segment 202 from a plurality of different channels, and the frequency controlled accordingly. In some instances, a first separate channel can introduce beads and a second separate channel can introduce analyte carriers into the channel segment 202. The first separate channel introducing the beads may be upstream or downstream of the second separate channel introducing the analyte carriers.

The second fluid 210 can comprise an oil, such as a fluorinated oil, that includes a fluorosurfactant for stabilizing the resulting droplets, for example, inhibiting subsequent coalescence of the resulting droplets.

In some instances, the second fluid 210 may not be subjected to and/or directed to any flow in or out of the reservoir 204. For example, the second fluid 210 may be substantially stationary in the reservoir 204. In some instances, the second fluid 210 may be subjected to flow within the reservoir 204, but not in or out of the reservoir 204, such as via application of pressure to the reservoir 204 and/or as affected by the incoming flow of the aqueous fluid 208 at the junction 206. Alternatively, the second fluid 210 may be subjected and/or directed to flow in or out of the reservoir 204. For example, the reservoir 204 can be a channel directing the second fluid 210 from upstream to downstream, transporting the generated droplets.

The channel structure 200 at or near the junction 206 may have certain geometric features that at least partly determine the sizes of the droplets formed by the channel structure 200. The channel segment 202 can have a height, $h_0$ and width, w, at or near the junction 206. By way of example, the channel segment 202 can comprise a rectangular cross-section that leads to a reservoir 204 having a wider cross-section (such as in width or diameter). Alternatively, the cross-section of the channel segment 202 can be other shapes, such as a circular shape, trapezoidal shape, polygonal shape, or any other shapes. The top and bottom walls of the reservoir 204 at or near the junction 206 can be inclined at an expansion angle, a. The expansion angle, a, allows the tongue (portion of the aqueous fluid 208 leaving channel segment 202 at junction 206 and entering the reservoir 204 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and a:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and a=3°, the predicted droplet size is 121 μm. In another example, for a channel structure with w=25 μm, h=25 μm, and a=5°, the predicted droplet size is 123 μm. In another example, for a channel structure with w=28 μm, h=28 μm, and a=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 208 entering the junction 206 can be between about 0.04 microliters (μL)/minute (min) and about 40 μL/min. In some instances, the flow rate of the aqueous fluid 208 entering the junction 206 can be between about 0.01 microliters (μL)/minute (min) and about 100 μL/min. Alternatively, the flow rate of the aqueous fluid 208 entering the junction 206 can be less than about 0.01 μL/min. Alternatively, the flow rate of the aqueous fluid 208 entering the junction 206 can be greater than about 40 μL/min, such as 45 μL/min, 50 μL/min, 55 μL/min, 60 μL/min, 65 L/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 208 entering the junction 206.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 206) between aqueous fluid 208 channel segments (e.g., channel segment 202) and the reservoir 204. Alternatively or in addition, the throughput of droplet generation can be increased by increasing the flow rate of the aqueous fluid 208 in the channel segment 202.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different analyte carrier or organism types within a population of analyte carriers, including, for example, microbiome analysis and characterization, environmental testing, food safety testing, epidemiological analysis, e.g., in tracing contamination or the like.

Computer Systems

Figure 14:
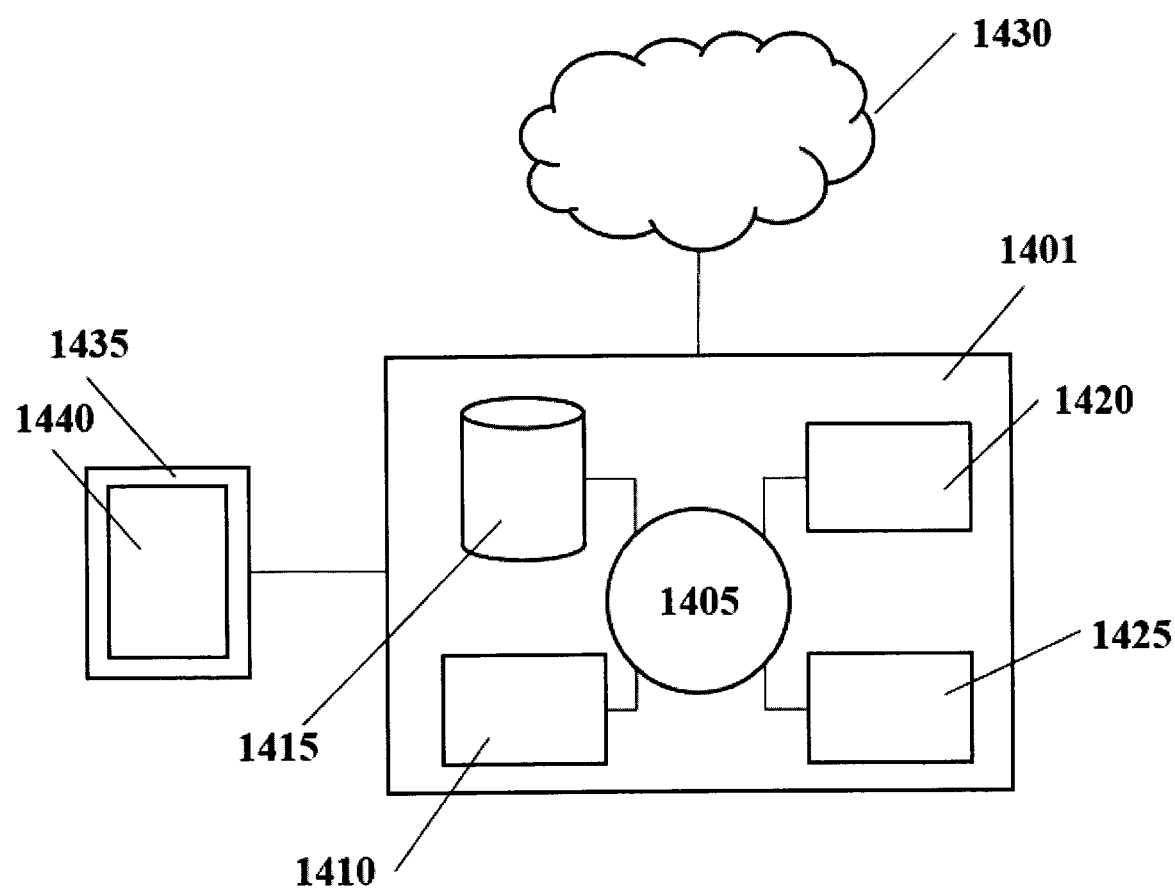
FIG. 14 shows a computer system that is programmed or otherwise configured to implement methods provided herein.

The present disclosure provides computer systems that are programmed to implement methods of the disclosure. FIG. 14 shows a computer system 1401 that is programmed or otherwise configured to (i) control a microfluidics system (e.g., fluid flow), (ii) sort occupied droplets from unoccupied droplets, (iii) polymerize droplets, (iv) perform sequencing applications, (v) generate and maintain a library of target nucleotides (e.g., introduce reactants and control reaction conditions), (vi) analyze sequences of target nucleotides. The computer system 1401 can regulate various aspects of the present disclosure, such as, for example, regulating fluid flow rate in one or more channels in a microfluidic structure, regulating polymerization application units, regulating reaction conditions, and regulating the introduction of reactants. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example, results of sequencing analysis. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, perform sequencing, control reaction temperature, control introduction of reactants, and control encapsulation of reactants and analytes.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, an analyte carrier (e.g., a cell or cell bead) is partitioned in a partition (e.g., droplet), and multiple analytes from the analyte carrier are processed for subsequent processing. The multiple analytes may be from the single cell. This may enable, for example, simultaneous proteomic, transcriptomic and genomic analysis of the cell.

Example 1: Preventing the Amplification of Artifactual Antisense Nucleic Acid Sequences First and second sets of partitions comprising a plurality of target mRNA molecules, a plurality of reverse transcriptases, a plurality of dNTPs, a plurality of reverse transcription template nucleic acid molecules and a bead attached to a plurality of barcode nucleic acid strands are prepared using the following protocol. First, a cryopreserved PBMC vial is thawed and measured to determine a volume needed to resuspend cells to achieve a 1000 cell load. Second, two sets of partitions are prepared with an enzyme and cell mixture supplemented with a dU-modified substitute gel bead oligo in the first set of partitions and a non-modified gel bead oligo in the second set of partitions. Reverse transcription and amplification are performed as outlined below.

In the first set of partitions, as can be seen in FIG. 10, the plurality of reverse transcription nucleic acid molecules comprise an amplification sequence 1007b and a poly-dT sequence 1007c that is configured to associate to a poly-A tail 1007a of a target mRNA molecule 1019. The barcode nucleic acid strands comprise a handle sequence 1002a comprising a modified nucleotide 1013, a unique molecular identifier 1004a, a barcode sequence 1003a, and a template switching sequence 1005a. The barcode nucleic acid strands comprise the following sequence: 5'-CTACACGACGCTC**CCGA*CT-NNNNNNNNNNNNNNNN-NNNNNNNNNNN-TTTCT-TATATrGrGrG-3'(SEQ ID NO: 1) wherein the asterisks represent modified nucleotides in the handle sequence 1013 (e.g., deoxyuridine), underlining represents a barcode sequence 1003a, italics represents a unique molecular identifier 1004a and bold represents a template switching sequence 1005a, 1006a.

First Set of Partitions

The target mRNA molecules 1019 are reverse transcribed using the plurality of reverse transcriptase and the plurality of reverse transcription template nucleic acid molecules to produce a plurality of reverse transcription products 1014. The barcode nucleic acid strands are then exposed to a stimulus that releases the barcode nucleic acid strands from the bead. The reverse transcription products 1014 then associate with the barcode nucleic acid strands 1015 and are extended using the barcode nucleic acid strands 1013 as a template to produce a plurality of extension products 1017. A cDNA amplification mix is introduced into the first partition. The cDNA amplification mix includes cDNA amplification reagents and USER II cleavage enzymes 1001 (uracil DNA glycosylase (UDG) and endonuclease VIII or endonuclease III). The first partition is incubated at 37° C. for 30 minutes to allow for the USER II cleavage enzymes 1001 cleave the barcode nucleic acid strands 1015 at the modified nucleotides 1017. The extension products 1017 are not cleaved. The partition is then cycled through temperatures of a polymerase chain reaction cycle to initiate the denaturation, annealing, and elongation using dNTPs, a DNA polymerase, a first primer 1008 comprising a sequence complementary to the handle sequence of the barcode nucleic acid molecule and a second primer 1009 comprising a sequence complementary to the amplification sequence of the extension product. The USER II cleavage enzymes 1001 are thermolabile and therefore substantially degraded upon the first PCR temperature cycle. The amplified extension products 812 as can be seen in FIG. 8 are then sequenced with a target sequencing depth of 20 k read-pairs per cell.

As can be seen in FIG. 15, step 1510, a target mRNA nucleic acid molecule 1519 can be mis-primed to a barcode nucleic acid strand and can be reverse transcribed to produce a mis-primed DNA nucleic acid molecule 1514. The target mRNA nucleic acid molecule 1519 can comprise a target sequence 1616 and a poly-A tail sequence 1507a. The mis-primed DNA nucleic acid molecule 1514 can comprise a whole or partial DNA complement of the target sequence 1516, a complement of a template switching sequence 1506b, a handle sequence 1502a, a barcode sequence 1503a, a unique molecular identifier 1504a, and/or a template switching sequence 1505a. In step 1511, the mis-primed DNA oligonucleotide 1514 can be associated with a barcode nucleic acid strand via the template switching rGrGrG sequence 1506a of the barcode nucleic acid strand and an extension reaction can be performed to produce an extension product 1517. The barcode nucleic acid strand can comprise a handle sequence 1502a, a barcode sequences 1503a, a unique molecular identifier 1504a, and/or a template switching sequence 1505a that comprises an rGrGrG sequence 1506a. The handle sequence 1502a comprises one or more modified nucleotides 1513 that are configured to be cleaved by a cleaving agent 1501. The extension product 1517 can comprise a complement of the handle sequence 1502b that does not comprise the modified nucleotide 1513, a complement of the barcode sequences 1503b, a complement of the unique molecular identifier 1504b, a complement of the template switching sequence 1505b that comprises a CCC sequence 1606b, the target DNA sequence 1516b, a handle sequence 1502a, a barcode sequences 1503a, a unique molecular identifier 1504a, and/or a template switching sequence 1505a that comprises a rGrGrG template switching sequence 1506a. In step 1512, the cleaving agent 1501 can cleave the handle sequence 1502*a* on both the barcode nucleic acid strand 1515 and the extension product 1517 to produce a cleaved extension product 1519. The cleaved extension product 1519 is not exponentially amplified since, while it contains a primer binding site for the first primer at one end, it has no primer binding site for either the first or second primer on the other end, as identified in FIG. 10.

Second Set of Partitions

In the second set of partitions, as can be seen in FIG. 16, a barcode nucleic acid strand 1615 can be provided. The barcode nucleic acid strand 1615 can be releasably attached to a bead 1601. The barcode nucleic acid strand 1615 can comprise a handle sequence 1602*a*, a barcode sequence 1603*a*, a unique molecular identifier 1604*a* and/or a template switching sequence 1605*a* that can further comprise a rGrGrG sequence 1606*a* configured to associate to a CCC sequence of a cDNA molecule. The barcode nucleic acid strands comprise the following sequence: 5'-CTA-CACGACGCTCTTCCGATCT-NNNNNNNNNNNNNNNN-NNNNNNNNNN-TTTCT-TATATrGrGrG-3'(SEQ ID NO: 2) wherein underlining represents a barcode sequence 1703*a*, italics represents a unique molecular identifier 1604*a* and bold represents a template switching sequence 1605*a*, 1606*a*. In step 1610, a reverse transcription sequence 1614 comprising a poly-dT sequence 1607*c* and a non-poly-dT sequence 1607*b* anneals to a target nucleic acid molecule 1619. The target nucleic acid molecule 1619 can be an mRNA molecule comprising a target sequence 1616*a* and a poly-A tail 1607*a*. In step 1611, the reverse transcription sequence 1614 can be extended along the length of the target nucleic acid molecule to produce a reverse transcription product 1617. The reverse transcription product 1617 comprises a sequence 1616*b* complementary to the target nucleic acid sequence 1616*a* and a template switching sequence 1606*b*. In step 1612, the reverse transcription product 1617 can be associated with a template switching sequence 1606*a* of the barcode nucleic acid molecule 1615. In step 1613, the reverse transcription product 1617 is extended to produce a first extension product 1619 that can include a complement of the barcode nucleic acid molecule 1615. The first extension product 1619 is then amplified using a primer complementary to the handle sequence 1602*b* and a sequence complementary to the non-poly-dT sequence 1607*b* to produce an amplification product 812 as can be seen in FIG. 8.

Also in the second set of partitions, as can be seen in FIG. 7, a barcode nucleic acid strand 715 can be provided. The barcode nucleic acid strand 715 can be releasably attached to a bead 701. The barcode nucleic acid strand 715 can comprise a handle sequence 702*a*, a barcode sequence 703*a*, a unique molecular identifier 704*a* and/or a template switching sequence 705*a* that can further comprise a rGrGrG sequence 706*a* configured to associate to a CCC sequence of a cDNA molecule. The barcode nucleic acid strands comprise the following sequence: 5'-CTA-CACGACGCTCTTCCGATCT-NNNNNNNNNNNNNNNN-NNNNNNNNNN-TTTCTTATATrGrGrG-3'(SEQ ID NO: 2) wherein underlining represents a barcode sequence 703*a*, italics represents a unique molecular identifier 704*a* and bold represents a template switching sequence 705*a*, 706*a*. In step 710, the barcode nucleic acid strand 715 can be released from the bead 701 and can mis-prime to a target nucleic acid molecule 716. The target nucleic acid molecule 716 can be an mRNA molecule comprising a target sequence 720*a* and a poly-A tail 707*a*. In step 711, the misprimed barcode nucleic acid strand 715 can be extended to produce a first mis-primed extension product 717 that can include a complement 720*b* of at least a portion of the target sequence 720*a*, and a CCC sequence 706*b* at a 3' end of the extension product. In step 712, the first mis-primed extension product 717 can be associated with a second barcode nucleic acid strand 718. In step 713, the extension product 717 can be extended to produce a second mis-primed extension product 719 that can include a complement (702*b*, 703*b*, 704*b*, 705*b*) of the second barcode nucleic acid strand 718 which comprises a different UMI sequence (e.g., BC-UMI-B) than the first barcode nucleic acid strand 715 (e.g., BC-UMI-A) In Step 714, the second mis-primed extension product 719 can be amplified using primers (708) that are complementary to the complement of the handle sequence to produce an amplification product 917 as can be seen in FIG. 9.

The first partition comprises amplified extension products 812 as can be seen in FIG. 8. The second partition comprises a mixture of amplified extension products 812 and 917 as can be seen in FIGS. 8 and 9, respectively. The amplified extension products 812/917 are then sequenced with a target sequencing depth of 20 k read-pairs per cell. The data is then analyzed in bulk. The sequencing results of amplified extension products 812 of the first partition has a lower percent of reads mapped antisense to a target gene than the sequencing results from the amplified extension products 812/917 of the second partition. Additional metrics measured are: Reads Mapped Confidently to Genome, Reads Mapped Confidently to Intergenic Regions, Reads Mapped Confidently to Intronic Regions, Reads Mapped Confidently to Exonic Regions, and Reads Mapped Confidently to the Transcriptome.

TABLE 1

Expected Results

| Cell Ranger Metric | Expected or desired behavior |
| --- | --- |
| Reads Mapped Confidently to Genome | No change or increased for dU-modified gel beads relative to non-modified gel beads |
| Reads Mapped Conf dently to Intergenic Regions | No change or decreased for dU-modified gel beads relative to non-modified gel beads |
| Reads Mapped Confidently to Intronic Regions | No change or decreased for dU-modified gel beads relative to non-modified gel beads |
| Reads Mapped Confidently to Exonic Regions | No change or increased for dU-modified gel beads relative to non-modified gel beads |
| Reads Mapped Confidently to Transcriptome | Increased for dU-modified gel beads relative to non-modified gel beads |

The sequencing data from the amplified extension products of the first set of partitions (containing dU-modified gel beads) is substantially free of antisense artifacts.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of nucleic acid processing, comprising:
   (a) providing a nucleic acid strand comprising a nucleic acid sequence associated with a barcode nucleic acid strand, wherein said barcode nucleic acid strand comprises a handle segment comprising a first sequence, and wherein said nucleic acid strand comprises a second sequence;
   (b) extending said nucleic acid strand of (a) using said handle segment of said barcode nucleic acid strand as a template to produce an extension product comprising said nucleic acid sequence and a first primer binding sequence, wherein said first primer binding sequence is complementary to said first sequence of said handle segment;
   (c) cleaving said first sequence in said handle segment of said barcode nucleic acid strand; and
   (d) amplifying said nucleic acid sequence using said extension product, a polymerase, a first primer that is hybridizable to said first primer binding sequence, and a second primer that is hybridizable to a second primer binding sequence having sequence complementarity to said second sequence to produce an amplification product comprising said nucleic acid sequence.

2. The method of claim 1, wherein said handle segment comprises one or more modified nucleotides, wherein said cleaving occurs at said one or more modified nucleotides.

3. The method of claim 2, wherein said one or more modified nucleotides are selected from the group consisting of deoxy uracil, thymine glycol, deoxyuridine, 5,6-dihydroxythymine, 5-hydroxy-5-methylhydantoin, uracil glycol, 6-hydroxy-5,6-dihydrothymine, 7,8-dihydro-8-oxoguanine, 8-oxoadenine, fapy-guanine, methyl-fapy-guanine, fapyadenine, aflatoxin B1-fapy-quanine, 5-hydroxy-cytosine, 5-hydroxyuracil, 5-hydroxymethyluracil, 5-formyluracil, is-syn cyclobutene pyrimidine dimer(s), 5,6-dihydrothymine, 5,6-dihydroxyuracil, 4,6-diamino-5-formamidopyrimidine, and 2,6-diamino-4-hydroxy-5-formamidopyrimidine.

4. The method of claim 2, wherein said cleaving is performed using a cleaving agent.

5. The method of claim 4, wherein said cleaving agent is an enzyme selected from the group consisting of: N-glycosylase, AP-lyase, uracil-DNA glycosylase (UDG), endonuclease VIII, Afu uracil-DNA glycosylase (UDG), antarctic thermolabile UDG, Tma endonuclease III, endonuclease IV, Tth endonuclease IV, endonuclease V, formamidopyrimidine DNA glycosylase (Fpg), human alkyl adenine DNA glycosylase (hAAG), hSMUG1, T4 PDG (T4 endonuclease V), hNEIL1, and hOGG1.

6. The method of claim 5, wherein said cleaving agent is formamidopyrimidine DNA glycosylase (Fpg), and said one or more modified nucleotides are selected from the group comprising: 7,8-dihydro-8-oxoguanine, 8-oxoadenine, fapy-guanine, fapy-adenine, aflatoxin, methyl-fapy-guanine, fapy-adenine, aflatoxin B1-fapy-guanine, 5-hydroxy-cytosine, and 5-hydroxy-uracil.

7. The method of claim 5, wherein said cleaving agent is human alkyl adenine DNA glycosylase (hAAG), and said one or more modified nucleotides are selected from the group comprising: 3-methyladenine, 7-methylguanine, 1,N6-ethenoadenine, hypoxanthine, deoxyinosine, and deoxyxanthosine.

8. The method of claim 4, wherein said cleaving agent comprises a temperature dependent cleaving agent.

9. The method of claim 5, wherein said cleaving agent is inactivated at a temperature greater than 65 degrees Celsius.

10. The method of claim 4, wherein said cleaving agent comprises (i) uracil DNA glycosylase (UDG), and (ii) endonuclease VIII or endonuclease III, and wherein said one or more modified nucleotides are selected from the group consisting of: deoxyuridine, urea, 5,6-dihydroxythymine, thymine glycol, 5-hydroxy-5-methylhydantoin, uracil glycol, and 6-hydroxy-5, 6-dihydrothymine.

11. The method of claim 1, wherein said nucleic acid strand is a complementary DNA (cDNA) strand comprising a cDNA sequence that is complementary to a target sequence in a template RNA molecule from a cell.

12. The method of claim 1, wherein (a) further comprises providing said barcode nucleic acid strand and a template RNA molecule from a cell in a partition among a plurality of partitions.

13. The method of claim 12, wherein (a) further comprises generating said [cDNA] nucleic acid strand by reverse transcribing said template RNA molecule.

14. The method of claim 13, wherein said reverse transcribing occurs after said barcode nucleic acid strand has been released from a bead.

15. The method of claim 1, wherein (a) comprises providing said nucleic acid strand associated with said barcode nucleic acid strand in a partition among a plurality of partitions.

16. The method of claim 15, wherein said partition is a droplet or a well.

17. A system comprising a reaction volume, comprising:
a nucleic acid molecule;
a barcode template switching oligonucleotide comprising a sequence complementary to a sequence of said nucleic acid molecule and a handle segment, wherein said handle segment comprises a first sequence comprising a modified nucleotide; and
a cleaving agent configured to cleave said handle segment of said barcode template switching oligonucleotide at said modified nucleotide; and
a first primer comprising said first sequence; and
a second primer comprising a second sequence in said nucleic acid molecule.

18. A kit comprising
a barcode template switching oligonucleotide comprising a barcode sequence, a sequence complementary to a sequence of a nucleic acid molecule, and a handle segment at a 5' end of said barcode template switching oligonucleotide, wherein said handle sequence segment comprises a first sequence comprising a modified nucleotide; and
a cleaving agent configured to cleave said handle segment at said modified nucleotide; and
a first primer comprising said first sequence; and
a second primer comprising a second sequence in said nucleic acid molecule.

19. The method of claim 1, wherein (a) further comprises providing a second nucleic acid strand associated with a second barcode nucleic acid strand, wherein said second barcode nucleic acid strand comprises a second handle segment, and wherein said second nucleic acid strand comprises a third handle segment.

20. The method of claim 19, wherein (b) further comprises extending said second nucleic acid strand using said second handle segment as a second template to produce a second extension product comprising said third handle segment.

21. The method of claim 20, wherein (c) further comprises (i) cleaving said second handle segment of said second barcode nucleic acid strand and (ii) cleaving said third handle segment of said second extension product.

22. The method of claim 21, wherein said handle segment, said second handle segment, and said third handle segment each comprises one or more modified nucleotides.

23. The method of claim 22, wherein said one or more modified nucleotides are selected from the group consisting of deoxy uracil, thymine glycol, deoxyuridine, 5,6-dihydroxythymine, 5-hydroxy-5-methylhydantoin, uracil glycol, 6-hydroxy-5,6-dihydrothymine, methyltartronylurea, 7,8-dihydro-8-oxoguanine, 8-oxoadenine, fapy-guanine, methyl-fapy-guanine, fapyadenine, aflatoxin B1-fapy-guanine, 5-hydroxy-cytosine, 5-hydroxyuracil, 5-hydroxymethyluracil, 5-formyluracil, is-syn cyclobutene pyrimidine dimer(s), 5,6-dihydrothymine, 5,6-dihydroxyuracil, 4,6-diamino-5-formamidopyrimidine, and 2,6-diamino-4-hydroxy-5-formamidopyrimidine.

24. The method of claim 23, wherein said second handle segment and said third handle segment comprise said first sequence.

25. The method of claim 24, wherein said first handle segment, said second handle segment, and said third handle segment are identical.

26. The method of claim 19, wherein said second handle segment and said third handle segment comprise said first sequence.

27. The method of claim 11, wherein said second sequence is on a 5' side of said cDNA sequence in said nucleic acid strand.

* * * * *